United States Patent

Franz et al.

Patent Number: 5,294,631
Date of Patent: Mar. 15, 1994

[54] SUBSTITUTED BENZIMIDAZOLES USEFUL AS ANGIOTENSION II RECEPTOR ANTAGONISTS

[75] Inventors: Robert G. Franz, Plymouth Meeting; Joseph Weinstock, Phoenixville, both of Pa.

[73] Assignee: SmithKline Beecham Corporation, Philadelphia, Pa.

[21] Appl. No.: 937,885

[22] PCT Filed: Apr. 8, 1991

[86] PCT No.: PCT/US 91/02396
§ 371 Date: Oct. 13, 1992
§ 102(e) Date: Oct. 13, 1992

Related U.S. Application Data

[63] Continuation-in-part of Ser. No. 509,268, Apr. 13, 1990, abandoned.

[51] Int. Cl.$^5$ .................. A61K 31/41; A61K 31/415; C07D 235/08; C07D 403/10
[52] U.S. Cl. .................. 514/381; 514/256; 514/339; 514/365; 514/383; 514/394; 544/333; 546/271; 548/181; 548/253; 548/266.4; 548/304.4; 548/304.7; 548/309.4; 548/309.7; 548/310.7
[58] Field of Search ........... 548/304.4, 304.7, 253, 548/309.4, 309.7, 310.7; 514/381, 394

[56] References Cited

U.S. PATENT DOCUMENTS

| | | | |
|---|---|---|---|
| 5,128,359 | 7/1992 | Bru-Magniez et al. | 514/394 |
| 5,177,074 | 1/1993 | Allen et al. | 514/234.2 |
| 5,179,112 | 1/1993 | Bernstein et al. | 514/359 |
| 5,191,086 | 3/1993 | Poss | 548/252 |

*Primary Examiner*—Joseph Paul Brust
*Assistant Examiner*—Mary Susan H. Gabilan
*Attorney, Agent, or Firm*—Mary E. McCarthy; Stephen Venetianer; Edward T. Lentz

[57] ABSTRACT

Angiotensin II receptor antagonists having the formula:

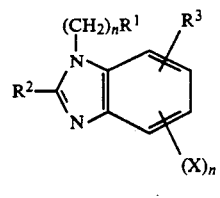

which are useful in regulating hypertension and in the treatment of congestive heart failure, renal failure, and glaucoma, pharmaceutical compositions including these antagonists, and methods of using these compounds to produce angiotensin II receptor antagonism in mammals.

20 Claims, No Drawings

SUBSTITUTED BENZIMIDAZOLES USEFUL AS ANGIOTENSION II RECEPTOR ANTAGONISTS

This application is a continuation-in-part of U.S. patent application Ser. No. 07/509,268, filed Apr. 13, 1990, now abandoned.

The present invention relates to new substituted benzimidazoles which are angiotensin II receptor antagonists and are useful in regulating hypertension induced or exacerbated by angiotensin II and in the treatment of congestive heart failure, renal failure, and glaucoma. This invention also relates to pharmaceutical compositions containing substituted benzimidazoles and methods for using these compounds as antagonists of angiotensin II, as anti-hypertensive agents and as agents for treating congestive heart failure, renal failure, and glaucoma.

BACKGROUND OF THE INVENTION

The class of peptide pressor hormone known as angiotensin is responsible for a vasopressor action that is implicated in the etiology of hypertension in man. Inappropriate activity of the renin-angiotensin systems appears to be a key element in essential hypertension, congestive heart failure and in some forms of renal disease. In addition to a direct action on arteries and arterioles, angiotensin II (AII), being one of the most potent endogenous vasoconstrictors known, stimulates the release of aldosterone from the adrenal cortex. Therefore, the renin-angiotensin system, by virtue of its participation in the control of renal sodium handling, plays an important role in cardiovascular homeostasis.

Interruption of the renin-angiotensin system with converting enzyme inhibitors, such as captopril, has proved to be clinically useful in the treatment of hypertension and congestive heart failure (Abrams, W. B., et al., (1984), *Federation Proc.,* 43, 1314). The most direct approach towards inhibition of the renin-angiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N. K., (1984), *J. Cardiovas. Pharmacol.,* 6, S176). In addition, recent animal studies suggest that inhibition of the renin-angiotensin system may be beneficial in halting or slowing the progression of chronic renal failure (Anderson, S., et al., (1985), *J. Clin. Invest.,* 76, 612). Also, a recent patent application (South African Patent Application Number 87/01,653) claims that AII antagonists are useful as agents for reducing and controlling elevated intraocular pressure, especially glaucoma, in mammals.

The compounds of this invention inhibit, block and antagonize the action of the hormone AII, and are therefore useful in regulating and moderating angiotensin induced hypertension, congestive heart failure, renal failure, glaucoma, and other disorders attributed to the actions of AII. When compounds of this invention are administered to mammals, the elevated blood pressure due to AII is reduced and other manifestations based on AII intercession are minimized and controlled. Compounds of this invention are also expected to exhibit diuretic activity.

Recognition of the importance of blocking and inhibiting the actions of AII has stimulated other efforts to synthesize antagonists of AII. The following references have disclosed imidazole derivatives which are described as having AII blocking activity and useful as hypotensive agents.

U.S. Pat. No. 4,340,598 discloses substituted imidazol-5-yl alkanoic acids and amido and lower-alkyl ester derivatives thereof, of the formula:

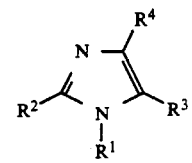

wherein $R^1$ is lower alkyl or phenyl$C_{1-2}$alkyl optionally substituted with halogen or nitro; $R^2$ is lower alkyl, cycloalkyl, or phenyl optionally substituted; one of $R^3$ and $R^4$ is —$(CH_2)_nCOR^5$, where $R^5$ is amino, lower alkoxy or hydroxy and n is 0–2, and the other of $R^3$ and $R^4$ is hydrogen or halogen. Examples include 1-benzyl-2-n-butyl-4-chloroimidazole-5-acetamide and 1-benzyl-2-n-butyl-5-chloroimidazole-4-acetic acid.

U.S. Pat. No. 4,355,040 disclosed substituted 1-benzylimidazol-5-yl acetic acid derivatives having the formula:

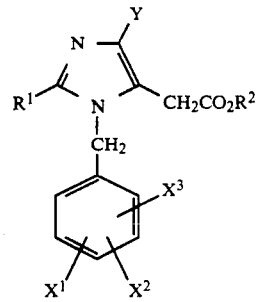

wherein $R^1$ is lower alkyl, cycloalkyl, or phenyl optionally substituted; $X^1, X^2$ and $X^3$ are each hydrogen, halogen, nitro, amino, lower alkyl, lower alkoxy, benzyloxy, or hydroxy; Y is halogen and $R^2$ is hydrogen or lower alkyl. A compound specifically disclosed is 1-(2-chlorobenzyl)-2-n-butyl-4-chloroimidazole-5-acetic acid.

European Patent Application 103,647 discloses substituted 1-benzyl-2-phenyl-4-chloro-imidazol-5-yl acetic acid derivatives of the formula:

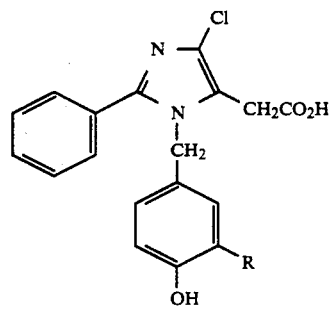

wherein R is lower alkyl. Specifically, the disclosure includes 4-chloro-1-(4-methoxy-3-methylbenzyl)-2-phenylimidazole-5-acetic acid.

European Patent Application 245,637 discloses substituted 4,5,6,7-tetrahydro-1H-imidazo[4,5-c]pyridine derivatives of the formula:

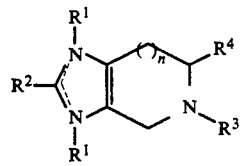

wherein ⎓ is a single or double bond; one of $R^1$ is present and includes groups such as $(CH_2)_{1-6}$naphthyl, $(CH_2)_{1-6}$heteroaryl, or $(CH_2)_{1-6}$Ph optionally substituted; $R^3$ includes groups such as $COC_{1-15}$alkyl or $(CH_2)_{1-6}$Ph optionally substituted; $R_4$ includes $CO_2R^9$, wherein $R^9$ is hydrogen, lower alkyl or benzyl; and n is 0–3. A compound specifically disclosed is 5-[(4-nitrophenyl)acetyl]-1-(phenylmethyl)-4,5,6,7-tetrahydro-1H-imidazo[4,5-c]pyridine-6-carboxylic acid.

European Patent Application 253,310 discloses substituted 1-aralkylimidazoles having the general formula:

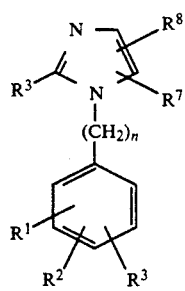

wherein $R^1$ includes groups such as phenyl optionally substituted or adamantylmethyl; $R^2$ includes groups such as hydrogen, halo, $NO_2$, $C_{1-4}$alkyl, or $C_{1-4}$alkoxy; $R^3$ is hydrogen, halo, $C_{1-4}$alkyl, or $C_{1-4}$alkoxy; $R^6$ includes groups such as $C_{2-10}$alkyl, $C_{3-10}$alkenyl, $C_{3-8}$cycloalkyl, benzyl optionally substituted or $Z(CH_2)_{1-5}$-$R^5$, wherein Z is O or S and $R^5$ is hydrogen, $C_{1-6}$alkyl, $C_{3-6}$cycloalkyl or alkenyl; $R^7$ is hydrogen, halo, $NO_2$, $CF_3$, or CN, and $R^8$ includes groups such as $C_{1-10}$alkanoic acids, esters and amides and alkyl N-alkyl carbamates. Examples include 2-n-butyl-5-chloro-1-(4-nitrobenzyl)imidazole-4-acetic acid and methyl 1-[(2'-carboxybiphenyl-4-yl)methyl]-2-butyl-4-chloroimidazole-5-carboxylate.

The following reference disclosed benzimidazole derivatives which are described as having AII receptor blocking activity.

U.S. Pat. No. 4,880,804 discloses substituted benzimidazoles having the formula:

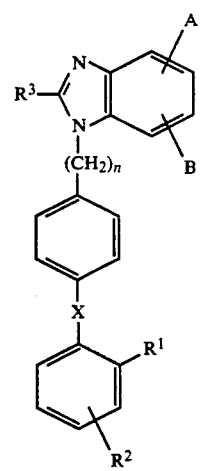

wherein $R^1$ is $CO_2H$, $NHSO_2CF_3$, or tetrazol-5-yl; $R^2$ is H, halo, $NO_2$, $OCH_3$, or $C_{1-4}$alkyl; $R^3$ is $C_{1-6}$alkyl, $C_{3-6}$alkenyl, or $C_{3-6}$alkynyl, each of which is optionally substituted by halo, $OR^4$, or $CO_2R^4$; $R^4$ is H or $C_{1-4}$alkyl; A includes groups such as H, $C_{1-10}$alkyl, halo, $C_{1-6}$alkoxy, $(CH_2)_nCOR^5$, $COR^5$, or $(CH_2)_nNHCO_2R^{10}$; B is H, $C_{1-10}$alkyl, halo, $C_{1-6}$alkoxy, $C_6F_5$, or $C_rF_{2r+1}$, where r is 1–6; $R^5$ includes groups such as OH or $OC_{1-5}$alkyl; $R^{10}$ is $C_{1-6}$alkyl; X is a carbon-carbon bond, CO, O, NHCO, or $OCH_2$; and n is 1 to 6. A compound specifically disclosed is 2-n-butyl-1-(2'-carboxybiphenyl-4-yl)methyl-6-chlorobenzimidazole.

DESCRIPTION OF THE INVENTION

The compounds of the present invention that are blockers of angiotensin II receptors are represented by the following Formula (I):

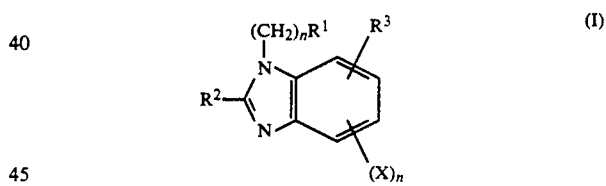

in which:

$R^1$ is —C(O)NH—CH(Y)—$(CH_2)_n$- aryl, —C(O)NH—CH(Y)—$(CH_2)_n$-heteroaryl, or phenyl unsubstituted or substituted by one to three substituents selected from Cl, Br, F, I, $C_{1-6}$alkyl, $C_{1-6}$alkoxy, OH, CN, $NO_2$, $CO_2R^4$, tetrazol-5-yl, $CONR^4R^4$, $SO_3H$, $C_mF_{2m+1}$, $SC_{1-6}$alkyl, or $SO_2C_{1-6}$alkyl;

$R^2$ is hydrogen, $C_{2-10}$alkyl, $C_{3-10}$alkenyl, $C_{3-6}$-cycloalkyl, $C_mF_{2m+1}$, or $(CH_2)_{0-8}$phenyl unsubstituted or substituted by one to three substituents selected from $C_{1-6}$alkyl, $C_{1-6}$alkoxy, Cl, Br, F, I, OH, $NO_2$, $C_mF_{2m+1}$, $CO_2R^4$, or $NR^4R^4$;

$R^3$ is —$(CH_2)_n$—Y, —CH=CY—$(CH_2)_n$-aryl, —CH=CY—$(CH_2)_n$-heteroaryl, —$(CH_2)_n$—C(O)—NH—CH(Y)—$(CH_2)_n$-aryl, —$(CH_2)_n$ —C(O)—NH—CH(Y)—$(CH_2)_n$heteroaryl, —$(CH_2)_m$—NH—CH(Y)—$(CH_2)_n$-aryl or —$(CH_2)_m$—NH—CH(Y)—$(CH_2)_n$-heteroaryl, when $R^1$ is an optionally substituted phenyl group; or H when $R^1$ is —C(O)NH—CH(Y)—$(CH_2)_n$-aryl or —C(O)NH—CH(Y)—$(CH_2)_n$-heteroaryl;

Y is $CO_2R^4$ or tetrazol-5-yl;

X is Cl, Br, F, I, $C_mF_{2m+1}$, $C_{1-6}$alkyl, $C_{1-6}$alkoxy, OH, O-phenyl, $CO_2R^4$, tetrazol-5-yl, CN, or $(CH_2)_{0-4}$phenyl unsubstituted or substituted by Cl, Br, F, I, $C_{1-6}$alkyl, $C_{1-6}$alkoxy, OH, $C_mF_{2m+1}$, CN, $CO_2R^4$, $NO_2$, or $NR^4R^4$;

aryl is phenyl, biphenyl, or naphthyl wherein each aryl group is unsubstituted or substituted by $C_{1-6}$alkyl, $C_{1-6}$alkoxy, Cl, Br, F, I, OH, $NO_2$, $CF_3$, $CO_2R^4$, or $NR^4R^4$;

heteroaryl is 2- or 3-thienyl, 2-, or 3-furanyl, 2-, 3-, or 4- pyridyl, pyrimidyl, imidazolyl, thiazolyl, triazolyl, or tetrazolyl wherein each heteroaryl group is unsubstituted or substituted by $C_{1-6}$alkyl, $C_{1-6}$alkoxy, Cl, Br, F, I, OH, $NO_2$, $CF_3$, $CO_2R^4$, or $NR^4R^4$;

each m independently is 1-3;
each n independently is 0-2; and
each $R^4$ independently is H or $C_{1-6}$alkyl; or a pharmaceutically acceptable salt thereof.

As used herein, the terms alkyl, alkenyl and alkoxy mean carbon chains which are branched or unbranched with the length of chain determined by the descriptor preceding the term.

Preferred compounds of the invention are represented by Formula (I) wherein:

$R^1$ is —C(O)NH—CH(Y)—$(CH_2)_n$-2-thienyl or phenyl unsubstituted or substituted by one to three substituents selected from chloro, fluoro, nitro, methyl, cyano, carbamoyl, trifluoromethyl, methoxy, tetrazol-5-yl, carboxy, carbo$C_{1-2}$alkoxy, or hydroxy;

$R^2$ is hydrogen, $C_{2-8}$alkyl or $C_mF_{2m+1}$;

X is absent or present as $CO_2H$, tetrazol-5-yl, Cl, Br, F, $CF_3$, $CH_3$, or $(CH_2)_{0-2}$phenyl taken once or twice;

$R^3$ is —$(CH_2)_n$—Y, —CH=CY—$(CH_2)_n$-2-thienyl, —$(CH_2)_n$—C(O)—NH—CH(Y)—$(CH_2)_n$-2-thienyl, or —$(CH_2)_m$—NH—CH(Y)—$(CH_2)_n$-2-thienyl, when $R^1$ is an optionally substituted phenyl group; or H when $R^1$ is C(O)NH—CH(Y)—$(CH_2)_n$-2-thienyl; and $R^4$, Y, m and n are as defined above; or a pharmaceutically acceptable salt thereof.

Particular compounds of the invention include, but are not limited to, the following:

2-n-butyl-1-(2-chlorophenyl)methyl-1H-benzimidazole-7-carboxylic acid;

5-bromo-2-n-butyl-1-(2-chlorophenyl)methyl-1H-benzimidazole-7-carboxylic acid;

2-n-butyl-6-chloro-1-(2-chlorophenyl)methyl-1H-benzimidazole-7-carboxylic acid;

2-n-butyl-1-(2-chlorophenyl)methyl-1H-benzimidazole-6-carboxylic acid;

2-n-butyl-5-phenyl-1-(2-chlorophenyl)methyl-1H-benzimidazole-7-carboxylic acid;

2-n-butyl-1-(2-chlorophenyl)methyl-7-(1H-tetrazol-5-yl)-1H-benzimidazole;

2-n-butyl-1-(2-chlorophenyl)methyl-1H-benzimidazole-5,7-dicarboxylic acid;

3-[2-n-butyl-1-(2-chlorophenyl)methyl-1H-benzimidazol-7-yl]-2-(2-thienyl)methyl-2-propenoic acid;

2-n-butyl-5,6-dichloro-1-(2-chlorophenyl)methyl-1H-benzimidazole-7-carboxylic acid;

2-[2-n-butyl-1-(2-chlorophenyl)methyl-1H-benzimidazol-7-yl]acetic acid;

L-α-amino-N-[2-n-butyl-1-(2-chlorophenyl)methyl-1H-benzimidazole-7-ethyl]-2-(2-thienyl)methylpropionic acid;

1-(2-chlorophenyl)methyl-2-heptafluoropropyl-1H-benzimidazole-6-carboxylic acid;

L-α-amino-N-(2-n-butyl-1H-benzimidazole-1-propanoyl)-2-(2-thienyl)methylpropanoic acid;

L-α-amino-N-(2-n-butyl-1H-benzimidazole-1-acetoyl)-2-(2-thienyl)methylpropionic acid;

L-α-N-[2-n-butyl-1-(2-chlorophenyl)methyl-1H-benzimidazole-7-acetoyl]-2-(2-thienyl)methylpropionic acid;

methyl L-α-amino-N-(2-n-butyl-1H-benzimidazole-1-propanoyl)-2-(2-thienyl)methylpropanoate;

2-n-butyl-1-(4-carboxyphenyl)methyl-5-chloro-1H-benzimidazole-7-carboxylic acid;

2-n-butyl-1-(4-carboxyphenyl)-5-chloro-1H-benzimidazole-7-carboxylic acid;

1-(4-carboxyphenyl)methyl-6-chloro-1H-benzimidazole-7-carboxylic acid;

2-n-butyl-1-(4-carboxyphenyl)ethyl-5-chloro-1H-benzimidazole-7-carboxylic acid;

2-n-butyl-1-(4-carboxyphenyl)methyl-5-chloro-4-methyl-1H-benzimidazole-7-carboxylic acid; or 2-n-butyl-5-chloro-1-(2-chlorophenyl)methyl-1H-benzimidazole-7-carboxylic acid; or a pharmaceutically acceptable salt thereof.

The invention also relates to pharmaceutical compositions comprising a pharmaceutical carrier and an effective amount of a compound of Formula (I).

Also included in the present invention are methods for antagonizing angiotensin II receptors which comprises administering to a subject in need thereof an effective amount of a compound of Formula (I). Methods of producing antihypertensive activity and methods of treating congestive heart failure, renal failure, and glaucoma by administering these compounds are also included in this invention.

The compounds of this invention and of the pharmaceutical compositions and methods of this invention are prepared by procedures described herein and illustrated by the examples. Reagents, protecting groups and functionality on the benzimidazole and other fragments of the molecule must be consistent with the proposed chemical transformations. Steps in the synthesis must be compatible with the functional groups and the protecting groups on the benzimidazole and other parts of the molecule.

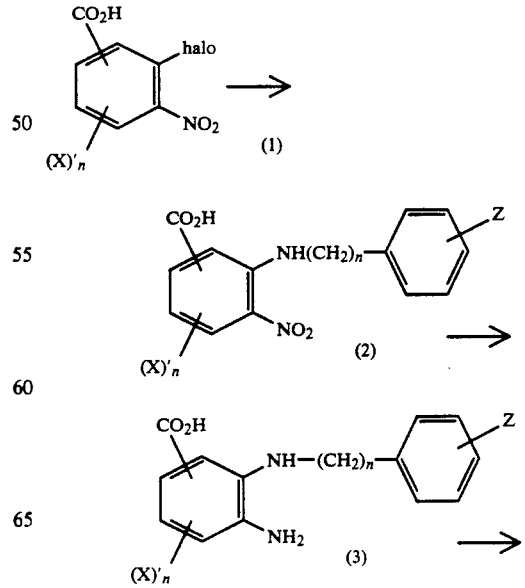

Scheme 1

-continued
Scheme 1

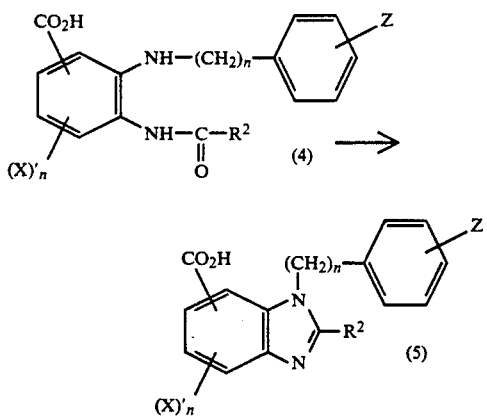

Scheme I shows the synthesis of Formula (I) compounds in which $R^1$ is a phenyl group substituted by one to three Z substituents selected from halo, $C_{1-6}$alkyl, $C_{1-6}$alkoxy, CN, $NO_2$, $CO_2R^4$, $SC_{1-6}$alkyl, $SO_2C_{1-6}$alkyl or $C_mF_{2m+1}$, wherein m is 1-3; $R^3$ is $CO_2H$; X' is halo, $C_{1-6}$alkyl, $C_{1-6}$alkoxy, $CO_2R^4$, optionally substituted $(CH_2)_{0-4}$phenyl, or $C_mF_{2m+1}$, wherein m is 1-3; and $R^2$, $R^4$ and n are as defined in Formula (I).

The starting nitrobenzoic acids of formula (1) are known to the art or are synthesized by known procedures. Formula (1) compounds have an activated leaving group, such as a halo substituent, which is displaced by an appropriately substituted phenyl-$(CH_2)_n$-amine, such as 2-chlorobenzylamine, in a suitable solvent, such as toluene, at a temperature from about 80° C. to 150° C., preferably at 110° C., to give formula (2) compounds. Alternately, formula (2) compounds are prepared by reacting formula (1) compounds with the appropriately substituted amine neat or in a suitable solvent, such as methanol or ethanol, in the presence of a base, such as potassium carbonate, in the absence or presence or a metal, such as copper. Formula (3) amine compounds are prepared by reduction of formula (2) nitro compounds, for example, using sodium hydrosulfite in the presence of a base, such as sodium bicarbonate, in a suitable solvent, such as tetrahydrofuran. The formula (3) amine compounds are converted to the corresponding amide derivatives of formula (4) in a reaction with an acyl halide, $R^2C(O)$halo wherein $R^2$ is as described in Formula I, in the presence of a suitable base or with an appropriately substituted acid, $R^2CO_2H$, in the presence of a suitable amide-forming reagent, such as N-hydroxysuccinimide or dicyclohexylcarbodiimide/1-hydroxybenzotriazole. The benzimidazole compounds of formula (5), which are Formula (I) compounds, are prepared by cyclization of formula (4) compounds in an acidic medium, for example, using acetic acid or a mixture of acetic acid and hydrochloric acid at a temperature from about 50° C. to 120° C., preferably at 95° C. Alternately, the formula (5) benzimidazole compounds are formed directly from formula (3) amine compounds in a reaction with an appropriately substituted anhydride, $(R^2CO)_2O$ or acid, $R^2CO_2H$.

Formula (5) compounds can also be prepared using the following procedure. Formula (2) amine compounds are acylated with an acyl halide, $R^2C(O)$halo, in the presence of a suitable base such as pyridine. The nitro group of this intermediate is then reduced to the corresponding amine compound using, for example, sodium hydrosulfide. Conversion to the formula (5) benzimidazole compounds is accomplished by cyclizing the amide-amine compounds under acidic conditions, for example, using a mixture of glacial acetic acid and hydrochloric acid.

Formula (I) benzimidazole carboxylic acid compounds can be converted to the corresponding $C_{1-6}$alkyl ester compounds using standard esterification techniques, such as gaseous hydrochloric acid in methanol.

Scheme II

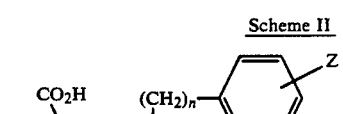

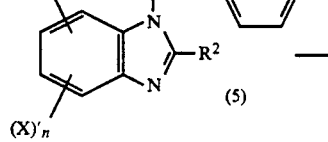

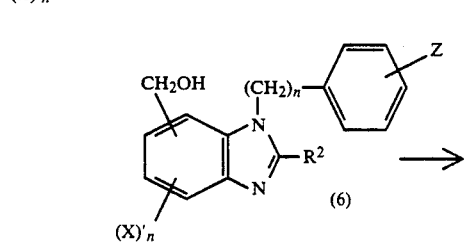

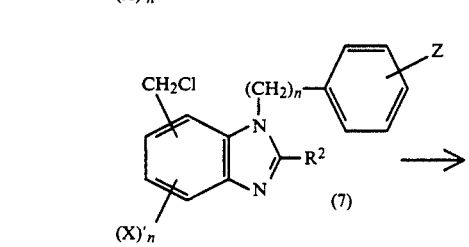

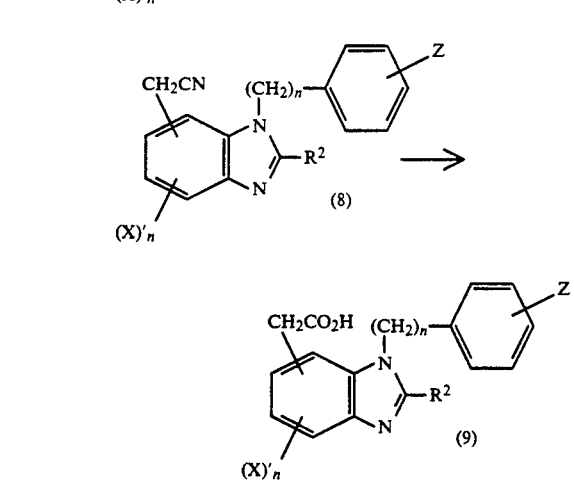

Scheme II shows the synthesis of Formula (I) compounds in which a methylene group is inserted between the phenyl portion of the benzimidazole nucleus and the carboxylic acid group of the formula (5), Scheme I, compounds. According to Scheme II, formula (6) hydroxymethyl compounds are prepared by reduction of the carboxylic acid moiety of the formula (5) compounds using a suitable reducing agent, such as diborane, in an inert solvent, such as tetrahydrofuran. The formula (6) compounds are converted to the corresponding chloromethyl compounds of formula (7) using a suitable chlorinating agent, such as thionyl chloride. Preparation of the formula (8) cyanomethyl compounds is accomplished by displacement of the chloro group of the formula (7) compounds, for example, using alkali metal cyanide, such as sodium cyanide, in a suitable solvent, such as dimethylsulfoxide. Acid hydrolysis of the formula (8) nitrile group, for example, using acetic acid in hydrochloric acid, gives formula (9) acid compounds, which are Formula (I) compounds.

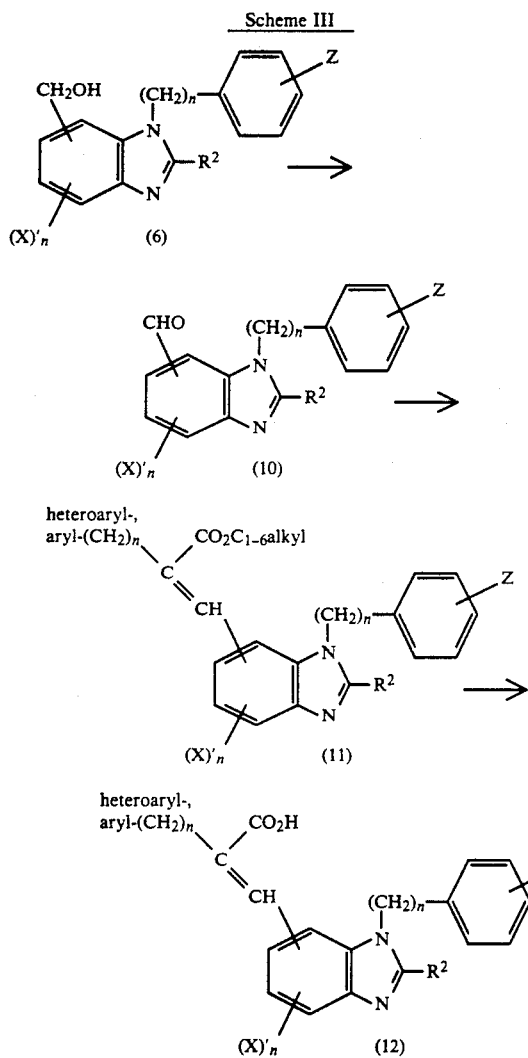

Scheme III

Scheme III shows the synthesis of Formula (I) compounds in which $R^3$ is $-CH=C(Y)'-(CH_2)_n$-aryl or $-CH=C(Y)'-(CH_2)_n$-heteroaryl, wherein $Y'$ is $CO_2R^4$ and Z, $X'$, n, $R^2$, aryl, and heteroaryl are as defined previously. According to Scheme III, the hydroxymethyl group of formula (6) compounds is oxidized to give formula (10) aldehyde compounds by treatment with a suitable reagent, such as anhydrous chromic acid-silica gel, or preferably, with activated manganese dioxide in a suitable solvent, such as toluene, at a temperature from about 25° C. to 115° C., preferably at 80° C. The formula (1) carboxaldehydes are treated with the lithium derivative of a substituted $C_{1-6}$alkyl ester. These lithio derivatives are prepared from the reaction of lithium diisopropylamide in a suitable solvent, such as tetrahydrofuran, with an acid ester, such as methyl 3-(2-thienyl)propanoate, to generate the α-lithio derivatives from about −78° C. to −10° C., preferably at −78° C., which are then treated with the formula (10) aldehyde compounds. The intermediate β-hydroxy group of the ester is converted to a mesylate or an acetate, and the mesylate, or preferably the acetate, is heated in a suitable solvent, such as toluene, with one or two equivalents of 1,8-diazobicyclo[5.4.0]undec-7-ene, from about 50° C. to 110° C., preferably at 80° C., to give formula (11) vinyl esters, which are Formula (I) compounds. These esters can be hydrolized to the corresponding Formula (I) acids of formula (12) using a base, such as potassium hydroxide or sodium hydroxide, in a suitable solvent system, such as aqueous alcohols or diglyme.

Alternatively, the Formula (I) compounds described in Scheme III are prepared by reacting the formula (10) aldehyde compounds with an appropriately substituted phosphonate to give formula (11) vinyl compounds directly. The phosphonates are prepared, for example, from trialkyl phosphonoacetates by alkylation with an appropriate halide, mesylate, or acetate in the presence of a suitable base, such as sodium hydride in a suitable solvent, such as diglyme, at a reaction temperature from about 25° C. to 110° C., preferably at 55° C., to provide the desired phosphonates, such as trimethyl 3-(2-thienyl)-2-phosphonopropionate. The reaction of the formula (10) aldehyde compounds with the phosphonates is performed in the presence of a suitable base, such as sodium methoxide or, preferably, sodium hydride, in a suitable solvent, such as methanol, tetrahydrofuran, or preferably diglyme, at a temperature from about 10° C. to 50° C., preferably at 25° C., to provide the formula (11) compounds. The formula (12) acid compounds are prepared from the formula (11) esters by the method described above.

Formula (I) compounds in which two methylene groups are present between the phenyl portion of the benzimidazole nucleus and the carboxlic acid group of the formula (5), Scheme I, compounds can be prepared from the formula (10) aldehyde compounds using the synthetic routes described for the preparation of formula (11) compounds. When the lithium anion route is followed, a $C_{1-6}$alkyl propanoate is used as the starting reagent in the reaction with the formula (10) aldehyde, while a trialkyl phosphonopropionate is the reagent of choice when the phosphonate route is used. The resulting vinyl esters are reduced to the corresponding saturated esters for example, using catalytic hydrogenation in a suitable solvent, such as ethanol, in the presence of an appropriate catalyst, such as palladium on carbon or platinum oxide, to give Formula (I) compounds wherein $R^3$ is $-(CH_2)_2CO_2C_{1-6}$alkyl. The corresponding Formula (I) acids are prepared from these esters by alkaline hydrolysis as described above.

Scheme IV

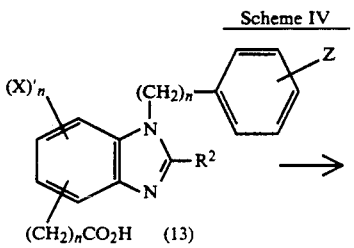

11

-continued
Scheme IV

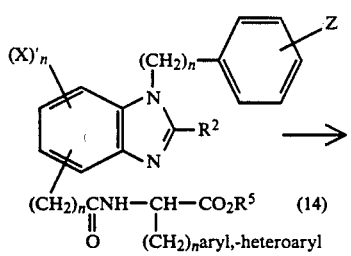
(14)

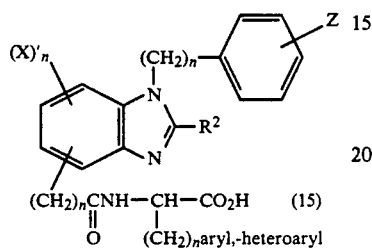
(15)

Scheme IV shows the synthesis of Formula (I) compounds in which $R^3$ is —$(CH_2)_n$—C(O)—NH—CH-(Y)—$(CH_2)_n$-aryl or —$(CH_2)_n$—C(O)—NH—CH-(Y)—$(CH_2)_n$-heteroaryl, wherein $R^2$, X',n, Z, aryl, and heteroaryl are as described previously and $R^5$ is $C_{1\text{-}6}$alkyl. According to Scheme IV, formula (13) compounds, which are Formula (I) compounds whose synthesis have been described hereinbefore, are reacted with an appropriately substituted amine, such as (2-thienyl)alanine methyl ester, in the presence of a suitable amide-forming reagent, such as N-hydroxysuccinimide or dicyclohexylcarbodiimide/1-hydroxybenzotriazole, in a suitable solvent, such as tetrahydrofuran or methylene chloride, to give the carboxamide compounds of formula (14). These Formula (I) ester compounds are converted to the corresponding acid compounds of formula (15), which are Formula (I) compounds, for examples by using a suitable aqueous base, such as aqueous potassium or sodium hydroxide in methanol or ethanol.

Scheme V

[structure with $(CH_2)_nCO_2H$ (13)]

[structure with $(CH_2)_nCH_2OH$ (16)]

12

-continued
Scheme V

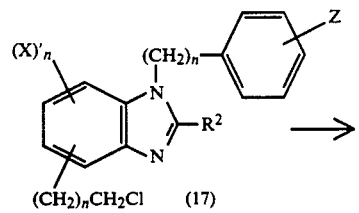
$(CH_2)_nCH_2Cl$ (17)

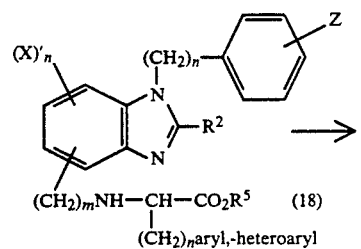
(18)

[structure with $(CH_2)_mNH$—CH—$CO_2H$ (19), $(CH_2)_n$aryl,-heteroaryl]

Scheme V shows the synthesis of Formula (I) compounds in which $R^3$ is —$(CH_2)_n$—NH—CH-(Y)—$(CH_2)_n$-aryl or —$(CH_2)_n$—C(O)—NH—CH-(Y)—$(CH_2)_n$-heteroaryl wherein $R^2$, X',Z, m, n, aryl, and heteroaryl are as described previously and $R^5$ is $C_{1\text{-}6}$alkyl. According to Scheme V, formula (13) compounds are converted to formula (16) hydroxyalkyl compounds and formula (17) chloroalkyl compounds in a manner which is as described for the conversion of formula (5) to formula (6) hydroxymethyl compounds and formula (7) chloromethyl compounds. Formula (17) chloroalkyl compounds are reacted with an appropriately substituted amine, such as (2-thienyl)alanine methyl ester, in the presence of a base, such as triethylamine, in a suitable solvent, such as dimethylformamide, at a temperature from about 0° C. to 110° C., preferably at 90° C., to give formula (18) ester compounds. These Formula (I) esters are hydrolyzed to the corresponding Formula (I) carboxylic esters of formula (19) with aqueous base, such as aqueous sodium or potassium hydroxide, in a suitable solvent, such as a lower alkyl alcohol, or with aqueous acid, such as aqueous hydrochloric acid.

The Formula (I) compounds wherein Y or X are tetrazol-5-yl are prepared by the following procedure. The Formula (I) carboxylic acid compounds prepared above are reacted with a halogenating agent, such as thionyl chloride, in a suitable solvent, such as methylene chloride, to give the corresponding acid halide compounds. The acid halides are then converted to primary amide compounds in a reaction with ammonium hydroxide. Subsequent dehydration of the amides with thionyl chloride yields the nitrile compounds, which are the immediate precursors to the Formula (I) tetrazole compounds. Tetrazole formation is accomplished by reacting the nitriles with azide, preferably tributyltin azide prepared in situ by the reaction of sodium azide with tributyltin chloride, in a suitable solvent, such as xylene.

Formula (I) compounds in which X is a phenyl group directly attached to the benzimidazole nucleus are prepared from the corresponding aryl halide, such as methyl 5-bromo-2-n-butyl-1-(2-chlorophenyl)methyl-1H-benzimidazole-7-carboxylate. This conversion involves reaction of the halo-benzimidazole with an optionally substituted phenylboronic acid in the presence of a phosphine ligand, such as tetrakis(triphenylphosphine)palladium(O), and a base, such as aqueous sodium carbonate, at a temperature from about 50° C. to 150° C., preferably at 80° C., in a suitable solvent, such as toluene. Alternately, the formula (I) aryl halides are employed to prepare Formula (I) compounds wherein X is $CO_2H$. The halo-benzimidazole is reacted with carbon monoxide in the presence of a phosphine ligand, such as triphenylphosphine, and a palladium reagnet, such as palladium chloride, in a suitable solvent, such as a mixture of benzene and dimethylformamide, to give formula (I) compounds wherein X is $CO_2H$.

Formula (I) compounds substituted by hydroxy are prepared from Formula (I) compounds which are substituted by $C_{1-6}$alkoxy using known hydrolysis methods, for example boron tribromide in a suitable solvent, such as methylene chloride, or aqueous hydrogen bromide.

Formula (I) compounds in which the substituent on the 1-$(CH_2)_n$-phenyl group is $CONR^4R^4$, wherein $R^4$ is hydrogen or $C_{1-4}$alkyl, are prepared from the corresponding carboxylic acid derivatives by treating the acid with a halogenating agent, such as thionyl chloride, followed by treatment with an appropriately substituted amine.

Scheme VI

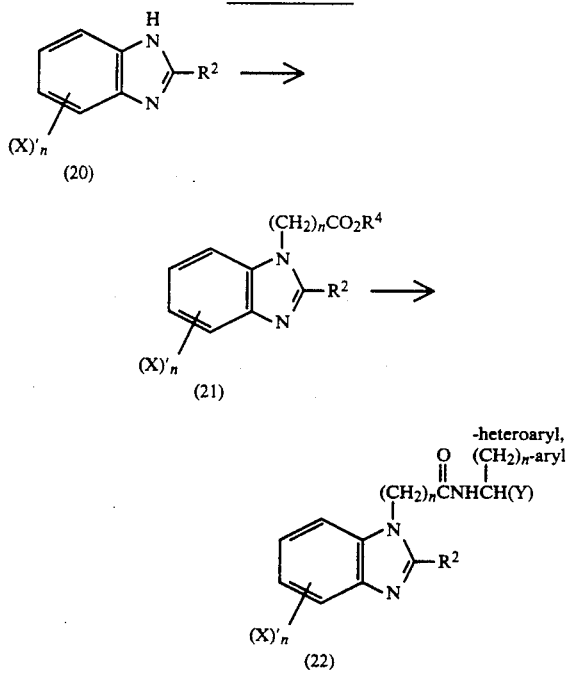

Scheme VI outlines the synthesis of Formula (I) compounds in which $R^1$ is —C(O)NH—CH(Y)—$(CH_2)_n$-aryl or —C(O)—NH—CH(Y)—$(CH_2)_n$-heteroaryl and $R^2$, $R^4$ X', n, aryl, and heteroaryl are as defined previously. According to Scheme VI, the starting 2-substituted benzimidazoles of formula (20), which are known in the art or are synthesized by known procedures, are alkylated at the 1-position for example, using neat acrylic acid at a temperature from about 120° C.–180° C., preferably at 150° C., or using a $C_{1-6}$alkyl ester of a haloalkenoate, such as ethyl bromoacetate, in the presence of a base, such as potassium carbonate, in a suitable solvent, such as dimethylformamide, to give formula (21) compounds. These intermediates, where necessary, are converted from $C_{1-6}$ alkyl ester compounds to the corresponding carboxylic acid derivatives for example using aqueous base, such as aqueous sodium or potassium hydroxide solution, in a suitable organic solvent, such as ethanol or methanol. The formula (21) acid compounds are reacted with amino acid esters, such as L-(2-thienyl)alanine methyl ester, or α-aralkyl(1H-tetrazol-5-yl)methanamines, such as α-(phenyl)methyl-α-(1H-tetrazol-5-yl)methanamine, in the presence of a suitable amide-forming reagent, such as N-hydroxysuccinimide or dicyclohexylcarbodiimide/1-hydroxybenzotriazole, in a suitable solvent, such as tetrahydrofuran or methylene chloride, to give the carboxamide compounds of formula (22), which are Formula (I) compounds in which Y is $CO_2C_{1-6}$alkyl or tetrazol-5-yl. The formula (22) $C_{1-6}$alkyl ester compounds are converted to the corresponding Formula (I) carboxylic acid compounds by basic hydrolysis, for example using aqueous sodium or potassium hydroxide solution in methanol or ethanol.

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent, such as ethanol, with isolation of the salt occurring by removal of the solvent or in an aqueous immiscible solvent when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric, and nitric acids.

Pharmaceutically acceptable base addition salts of compounds of Formula (I) are prepared from carboxy substituted compounds by known methods from organic and inorganic bases, including non-toxic alkali metal and alkaline earth bases, for example, calcium, lithium, sodium, and potassium hydroxide; ammonium hydroxide, and non-toxic organic bases such as triethylamine, dicyclohexylamine, butylamine, piperazine, meglumine, choline, diethanolamine, and tromethamine.

Angiotensin II antagonist activity of the compounds of Formulas (I) is assessed by in vitro and in vivo methods. In vitro antagonist activity is determined by the ability of the compounds to compete with $^{125}I$-angiotensin II for binding to vascular angiotensin II receptors and by their ability to antagonize the contractile response to angiotensin II in the isolated rabbit aorta. In vivo activity is evaluated by the efficacy of the compounds to inhibit the pressor response to exogenous angiotensin II in conscious rats and to lower blood pressure in a rat model of renin dependent hypertension.

Binding

The radioligand binding assay is a modification of a method previously described in detail (Gunther et al., Circ. Res. 47:278, 1980). A particular fraction from rat mesenteric arteries is incubated in Tris buffer with 80 pm of $^{125}$I angiotensin II with or without angiotensin II antagonists for 1 hour at 25° C. The incubation is terminated by rapid filtration and receptor bound $^{125}$I-angiotensin II trapped on the filter is quantitated with a gamma counter. The potency of angiotensin II antagonists is expressed as the $IC_{50}$ which is the concentration of antagonist needed to displace 50% of the total specifically bound angiotensin II. Exemplary of the $IC_{50}$ of compounds of the invention is about 0.1 to about 50 $\mu M$.

Aorta

The ability of the compounds to antagonize angiotensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist dissociation constants ($K_B$) are calculated by the dose ratio method using the mean effective concentrations. Exemplary of the $K_B$ of compounds of the invention is about 0.01 to about 50 $\mu M$.

Inhibition of pressor response to angiotensin II in conscious rats

Rats are prepared with indwelling femoral arterial and venous catheters and a stomach tube (Gellai et al., Kidney Int. 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 3 to 300 mg/kg. The dose of compound needed to produce 50% inhibition of the control response to angiotensin II ($IC_{50}$) is used to estimate the potency of the compounds. The $IC_{50}$ of 2-n-butyl-6-chloro-1-(2-chlorophenyl)methyl-1H-benzimidazole-7-carboxylic acid is 16 mg/kg i.v. and 31 mg/kg orally.

Antihypertensive activity

The antihypertensive activity of the compounds is measured by their ability to reduce mean arterial pressure in conscious rats made renin-dependent hypertensive by ligation of the left renal artery (Cangiano et al.,J. Pharmacol. Exp. Ther. 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intravenously or orally. The dose of compound needed to reduce mean arterial pressure by 30 mm Hg ($IC_{30}$) is used as an estimate of potency. The $IC_{30}$ of 5-bromo-2-n-butyl-1-(2-chlorophenyl)methyl-1H-benzimidazole-7-carboxylic acid is 32 mg/kg orally.

The intraocular pressure lowering effects employed in this invention may be measured by the procedure described by Watkins, et al., J. Ocular Pharmacol., 1 (2):161–168 (1985).

The compounds of Formula (I) are incorporated into convenient dosage forms, such as injectable preparations, or for orally active compounds, capsules or tablets. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies but, preferably, will be from about 25 mg to about 1 g per dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

For topical ophthalmologic administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmaceutical preparation may also contain non-toxic auxiliary substances such as emulsifying, preserving, wetting, and bodying agents, as for example, polyethylene glycols; antibacterial components such as quaternary ammonium compounds; buffering ingredients such as alkali metal chloride; antioxidants such as sodium metabisulfite; and other conventional ingredients such as sorbitan monolaurate.

In addition, suitable ophthalmic vehicles may be used as carrier media for the present purpose including conventional phosphate buffer vehicle systems.

The pharmaceutical preparation may also be in the form of a solid insert. For example, one may use a solid water soluble polymer as the carrier for the medicament. Solid water insoluble inserts, such as those prepared from ethylene vinyl acetate copolymer, may also be utilized.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, or topical products.

Doses of the compounds of Formula (I) in a pharmaceutical dosage unit as described above will be an efficacious, non-toxic quantity selected from the range of 0.01–200 mg/kg of active compound, preferably 0.1–100 mg/kg. The selected dose is administered to a human patient in need of angiotensin receptor antagonism from 1–6 times daily, orally, rectally, topically by injection, or continuously by infusion. Oral dosage units for human administration preferably contain from 10 to 500 mg of active compound. Lower dosages are used generally for parenteral administration. Oral administration is used when safe, effective and convenient for the patient. Topical formulations contain the active compound in an amount selected from 0.0001 to 0.1

(w/v %), preferably 0.0001 to 0.01. As a topical dosage unit form, an amount of active compound from between 50 mg to 0.05 mg, preferably 50 mg to 5 mg is applied to the human eye.

The method of this invention of antagonizing angiotensin II receptors in mammals, including humans, comprises administering to a subject in need of such antagonism an effective amount of a compound of Formula (I). The method of this invention of producing antihypertensive activity and the methods of treating congestive heart failure, glaucoma, and renal failure comprise administering a compound of Formula (I) to a subject in need of the indicated activity in an effective amount to produce said activity.

The following examples illustrate preparation of compounds and pharmaceutical compositions of this invention. The examples are not intended to limit the scope of this invention as defined hereinabove and as claimed below.

Example 1

5-Bromo-2-n-butyl-1-(2-chlorophenyl)methyl-1H-benzimidazole-7-carboxylic Acid (i) 2,5-dibromo-3-nitrobenzoic acid The procedure described in R. K. Bentley and F. G. Holliman, *J. Chem. Soc.* (c), 2447 (1970) was used. A mixture of 2,5-dibromobenzoic acid (50 g, 0.18 mol) in concentrated sulfuric acid was vigorously stirred as fuming nitric acid (62.5 mL) was added dropwise at a rate to keep the temperature below 70° C. The reaction mixture was vigorously stirred, heated to 100° C. and then kept at 100° C. for 5 hours. The cooled reaction was cautiously poured into 2 liters of ice and vigorously stirred, the precipitate was filtered through a sintered glass funnel and the solid was washed well with water. Crystallization was achieved by dissolving the solid in acetic acid (150 mL) and after concentration to a half of the volume, crystals separated (16.72 g); mp 225°–229° C. An additional crop of 7.52 g was obtained to give a total yield of 24.24 g (41%).

(ii) 5-bromo-2-[(2-chlorophenyl)-methyl]amino-3-nitrobenzoic acid

A suspension of 2,5-dibromo-3-nitrobenzoic acid (10.76 g, 0.0331 mol) in toluene (100 mL) was placed under argon, treated with 2-chlorobenzylamine (14.06 g, 0.0993 mol) and the mixture was brought to reflux. A clear, red solution resulted and the solution was refluxed for 24 hours, cooled, poured into 5% sodium hydroxide solution (600 mL) and ether (100 mL). The insoluble material was filtered off, the layers separated and the aqueous phase was added to the insoluble material and acidified with 10% hydrochloric acid solution. The separated crystalline product was collected, washed with water and the solid was crystallized from a large volume of methanol to provide 7.85 g (61.5%) of the yellow crystalline 5-bromo-2-[(2-chlorophenyl)methyl]amino-3-nitrobenzoic acid; mp 159°–161° C.

(iii) 5-bromo-2-[(2-chlorophenyl)methyl-N-valeryl]amino-3-nitrobenzoic acid

A solution of 5-bromo-2-[(2-chlorophenyl)methyl]-amino-3-nitrobenzoic acid (8 g, 0.021 mmol) in pyridine (100 mL) was cooled in ice under argon and valeryl chloride (5.5 g, 0.046 mol) was added. The mixture was heated at 45° C. for 18 hours, poured into water, acidified with hydrochloric acid and the oily product was extracted into ethyl acetate. The organic extracts were washed with 10% hydrochloric acid solution and brine, and the dried, concentrated product afforded about 100% yield of the crude oil, 5-bromo-2-[(2-chlorophenyl)methyl-N-valeryl]-amino-3-nitrobenzoic acid, which was used without further purification.

(iv) 5-bromo-2-n-butyl-1-(2-chlorophenyl)methyl-1H-benzimidazole-7-carboxylic acid A solution of 5-bromo-2-[(2-chlorophenyl)methyl-N-valeryl]amino-3-nitrobenzoic acid (9.72 g, 0.0207 mol) in tetrahydrofuran (75 mL) was diluted with 5% sodium bicarbonate solution (75 mL), and then treated portionwise with sodium hydrosulfite (12 g) over 2 hours. The pH was adjusted to 7.1 with additional solid sodium bicarbonate. After an hour of stirring, 6 g of additional sodium hydrosulfite was added, and, after another hour of stirring, the mixture was filtered, diluted with ether, and the layers were separated. The organic phase was concentrated to a solid that was dissolved in acetic acid (15 mL) and concentrated hydrochloric acid (5 mL) and heated on a steam bath for 2 hours. The residual slurry was concentrated in vacuo, diluted with water and the solid was collected. The solid was dissolved in hot methanol, some insolubles filtered off, and the filtrate was concentrated to incipient crystallization. After chilling, there was obtained 4.26 g (37%) of 5-bromo-2-n-butyl-1-(2-chlorophenyl)methyl-1H-benzimidazole-7-carboxylic acid; mp 254°–255° C.

Example 2

2-n-Butyl-1-(2-chlorophenyl)methyl-1H-benzimidazole-6-carboxylic Acid (i) 3-[(2-chlorophenyl)methyl]-amino-4-nitrobenzoic acid The procedure of Example 1(ii) was followed. From 6.25 g (33.8 mmol) of 3-fluoro-4-nitrobenzoic acid (mp 168°–169° C.; prepared by the method of F. C. Schmelkes and M. Rubin, *J.A.C.S.*, 66, 1631 (1944), by permanganate oxidation of 3-fluoro-4-nitrotoluene) 11.96 g (84.5 mmol) of 2-chlorobenzylamine and 100 mL of toluene refluxed for 24 hours was obtained, after workup and crystallization from methanol, 8.4 g (82%) of 3-[(2-chlorophenyl)methyl]-amino-4-nitrobenzoic acid; mp 221°–223° C.

(ii) 4-amino-3-[(2-chlorophenyl)methyl]aminobenzoic acid

A mixture of 3-[(2-chlorophenyl)methyl]amino-4-nitrobenzoic acid (6 g, 19.6 mmol), tetrahydrofuran (60 mL) and 5% sodium bicarbonate solution (50 mL) was treated portionwise with sodium hydrosulfite (4 g). The resulting clear solution had a pH of 6.29 that was adjusted to pH 7.15 by the addition of solid sodium bicarbonate. Additional sodium hydrosulfite was added (12 g) over several hours, and the mixture was stirred overnight. The tetrahydrofuran phase was separated, concentrated and triturated with ether/methylene chloride/hexane to afford 5.07 g of solid. Crystallization from methanol followed by washing with cold dilute aqueous methanol provided 4.79 g (88%) of pink-to-white crystals of 4-amino-3-[(2-chlorophenyl)methyl]aminobenzoic acid; mp 176°–177° C.

(iii) 3-[(2-chlorophenyl)methyl]amino-4-(valeryl)-aminobenzoic acid

A solution of 4-amino-3-[(2-chlorophenyl)methyl]-aminobenzoic acid (2.75 g, 9.95 mmol) in pyridine (80 mL) was cooled in ice water as valeryl chloride (1.32 g, 10.9 mmol) was added. The mixture was stirred at room temperature for 2.5 hours, poured onto ice and acidified with concentrated hydrochloric acid. The resulting suspension was chilled, filtered and the solid was washed well with water to give 2.85 g of crude product; mp 193°-194° C. (d). Crystallization from methanol gave the white crystalline 3-[(2-chlorophenyl)methyl]amino-4-(valeryl)aminobenzoic acid (2.71 g, 76%); mp 202° C. (d).

(iv) 2-n-butyl-1-(2-chlorophenyl)methyl-1H-benzimidazole-6-carboxylic acid

A solution of 3-[(2-chlorophenyl)methyl]amino-4-(valeryl)aminobenzoic acid (1.5 g, 4.16 mmol) in glacial acetic acid (10 mL) was refluxed for 5 hours, cooled, diluted with water (75 mL), and the crystals that separated were filtered, washed with water and dried to afford 1.33 g of crude product. Crystallization from methanol gave 1.24 g (87%) of 2-n-butyl-1-(2-chlorophenyl)methyl-1H-benzimidazole-6-carboxylic acid; mp 238°-241° C.

Example 3

2-n-Butyl-1-(2-chlorophenyl)methyl-1H-benzimidazole-7-carboxylic Acid (i) 2-[(2-chlorophenyl)methyl]amino-3-nitrobenzoic acid The procedure of Example 1(ii) was followed using 2-chloro-3-nitrobenzoic acid in place of 2,5-dibromo-3-nitrobenzoic acid. The title compound was a pale yellow crystalline material, obtained in 63% yield; mp 164°-164.5° C.

ii) 2-n-butyl-1-(2-chlorophenyl)methyl-1H-benzimidazole-7-carboxylic acid

Method A. A solution of 2-[(2-chlorophenyl)-methyl]amino-3-nitrobenzoic acid (15.62 g, 0.051 mol) in pyridine (125 mL) was stirred with valeryl chloride (15.37 g, 0.127 mol) at 52° C. for 18 hours under argon. The usual workup gave the crude 2-[(2-chlorophenyl)methyl-N-valeryl]-amino-3-nitrobenzoic acid which was not purified. This benzoic acid (51 mmol) was dissolved in tetrahydrofuran (250 mL) and 5% sodium bicarbonate solution (250 mL) was added to give a pH of 7.41. Sodium hydrosulfite (7 times 15 g portions) was added over 3 hours with the pH being adjusted to 7.1 with solid sodium bicarbonate. The mixture was filtered, some ether was added and the organic layer was washed with brine, stirred over magnesium sulfate, filtered and concentrated to a slurry. This crude aminobenzoic acid (23.9 g) was dissolved in a mixture of acetic acid (120 mL) and concentrated hydrochloric acid (40 mL) and heated on a steam bath for 1.5 hours. The solvents were removed in vacuo, and ice water was added to the residue. The precipitated crystals were filtered, washed with water and dried to provide 12.04 g of crude product. Crystallization from methanol gave 9.1 g of 2-n-butyl-1-(2-chlorophenyl)-methyl-1H-benzimidazole-7-carboxylic acid; mp 253°-255° C.

Method B. 2-[(2-chlorophenyl)methyl]amino-3-nitrobenzoic acid (22 g, 72 mmol) was reduced with sodium hydrosulfite by the method described in Example 2(ii) to provide 3-amino-2-[(2-chlorophenyl)methyl]aminobenzoic acid in 85% yield; mp 203°-204° C. This amine was acylated with excess valeryl chloride in the presence of excess 10% sodium hydroxide solution and toluene. The resulting valeryl derivative was heated in acetic acid and hydrochloric acid according to the procedure described in Method A to provide the title compound.

Example 4

2-n-Butyl-1-(2-chlorophenyl)methyl-1H-benzimidazole-5-carboxylic Acid (i) 4-[(2-chlorophenyl)methyl]-amino-3-nitrobenzoic acid The procedure of Example 1(ii) was followed. From 5.0 g (24.8 mmol) of 4-chloro-3-nitrobenzoic acid and proportional quantities of other reagents was obtained 4.26 g (56%) of 4-[(2-chlorophenyl)methyl]amino-3-nitro-benzoic acid; mp 250°-251° C. (from methanol).

(ii) 3-amino-4-[(2-chlorophenyl)-methyl]aminobenzoic acid

The procedure of Example 2(ii) was followed. From 3.06 (10 mmol) of 4-[(2-chlorophenyl)methyl]amino-3-nitrobenzoic acid in 30 mL of tetrahydrofuran, 25 mL of 5% sodium bicarbonate solution and excess sodium sulfite was obtained 1.93 g (70%) of 3-amino-4-[(2-chlorophenyl)-methyl]aminobenzoic acid; mp 180°-181° C. (from ethyl acetate/hexane).

(iii) 2-n-butyl-1-(2-chlorophenyl)methyl-1H-benzimidazole-5-carboxylic acid

The procedure of example 2(iii) was followed to prepare the amide, 4-[(2-chlorophenyl)methyl]amino-3-(valeryl)aminobenzoic acid, from 3-amino-4-[(2-chlorophenyl)methyl]aminobenzoic acid. The valeryl amide melted at 207°-209° C. (from ethyl acetate/hexane). This amide (0.39 g, 1.08 mmol) was refluxed in acetic acid (2.5 mL) for 3 hours, the acetic acid was evaporated, water was added and the resulting solid was filtered and washed with water. Crystallization from methanol provided 0.3 g (81%) of 2-n-butyl-1-(2-chlorophenyl)methyl-1H-benzimidazole-5-carboxylic acid; mp 238°-239° C.

Example 5

2-n-Butyl-1-(2-chlorophenyl)methyl-7-(1H-tetrazol-5-yl)-1H-benzimidazole (i) 2-n-butyl-7-carboxamido-1-(2-chlorophenyl)methyl-1H-benzimidazole To a solution of 2-n-butyl-1-(2-chlorophenyl)-methyl-1H-benzimidazole-7-carboxylic acid (Example 3) (5.29 g, 15.4 mmol) in methylene chloride (50 mL) was added thionyl chloride (2.25 mL, 31 mmol). The mixture was stirred at ambient temperature for 3.5 hours, and then poured into iced ammonium hydroxide solution% The two phase suspension was concentrated in vacuo, the resulting aqueous suspension was filtered to give a solid. The dried solid was crystallized from chloroform/hexane to provide 2.64 g (50%) of 2-n-butyl-7-carboxamido-1-(2-chlorophenyl)methyl-1H-benzimidazole; mp 185.5°-186.5° C.

(ii) 2-n-butyl-1-(2-chlorophenyl)methyl-7-cyano-1H-benzimidazole

A mixture of 2-n-butyl-7-carboxamido-1-(2-chlorophenyl)methyl-1H-benzimidazole (0.5 g, 1.46 mmol) and thionyl chloride (1.06 mL, 14.6 mmol) was refluxed under argon for 5 hours. The solvent was evaporated and the residue was chromatographed over silica gel with chloroform to give 130 mg of 2-n-butyl-1-(2-chlorophenyl)methyl-7-cyano-1H-benzimidazole; mp 124°-127° C.

(iii) 2-n-butyl-1-(2-chlorophenyl)methyl-7-(1H-tetrazol-5-yl)-1H-benzimidazole

A mixture of 2-n-butyl-1-(2-chlorophenyl)methyl-7-cyano-1H-benzimidazole (0.72 g, 2.22 mmol) in xylene (10 mL) was treated with tributyltin azide (prepared by stirring sodium azide (0.325 g, 5 mmol) dissolved in water (0.25 mL) in an ice bath and adding tributyltin chloride (1.25 g, 3.33 mmol) for 2 hours, followed by extraction of the resulting tributyltin azide into methylene chloride which was dried (magnesium sulfate) and concentrated to give the product as an oil; method described in K. R. Kricheldorf and E. Leppert, Synthesis, 329 (1976)). The mixture was heated to reflux for 8 hours, the xylene was evaporated and the residual product was acidified with ethereal hydrochloric acid. The solid was boiled in chloroform, cooled and filtered to afford 0.62 g (69%) of the hydrochloride salt of 2-n-butyl-1-(2-chlorophenyl)methyl-7-(1H-tetrazol-5-yl)-1H-benzimidzaole; mp 215°-218° C.

Example 6

2-n-Butyl-1-(2-chlorolphenyl)methyl-5-phenyl-1H-benzimidazole-7-carboxylic Acid (i) methyl 5-bromo-2-n-butyl-1-(2-chlorophenyl)-methyl-1H-benzimidazole-7-carboxylate A mixture of 5-bromo-2-n-butyl-1-(2-chlorophenyl)-methyl-1H-benzimidazole-7-carboxylic acid (prepared in Example 1)(1.0 g, 2.4 mmol) in methanol (15 mL) was cooled in ice and then saturated with dry hydrochloric acid. The reaction mixture was refluxed for 14 hours, and TLC on silica with 9:1 chloroform/methanol containing a trace of formic acid gave an $R_f$ 0.87 for the product; the starting material had an $R_f$ 0.65. The methanol was evaporated, the residue was diluted with ice water and the solid was separated, washed with water and dried at 92° C. at high vacuum to provide 0.88 g of methyl 5-bromo-2-n-butyl-1-(2-chlorophenyl)methyl-1H-benzimidazole-7-carboxylate.

(ii) methyl 2-n-butyl-1-(2-chlorophenyl)methyl-5-phenyl-1H-benzimidazole-7-carboxylate A mixture of methyl 5-bromo-2-n-butyl-1-(2-chlorophenyl)methyl-1H-benzimidazole-7-carboxylate (600 mg, 1.38 mmol), tetrakis(triphenylphosphine)palladium(O) (50 mg), toluene (3 mL) and 2M sodium carbonate solution (1.5 mL) was treated with a solution of phenylboronic acid (200 mg, 1.64 mmol) in methanol (0.3 mL). The resulting mixture was vigorously stirred under an argon atmosphere and heated at 80° C. for 18 hours. The cooled reaction was diluted with methylene chloride, 2M sodium carbonate solution and a few drops of ammonium hydroxide solution. Some insolubles were filtered, the organic phase was separated, dried (magnesium sulfate) and concentrated to 0.55 g of crude product. TLC on silica with 4:1 hexane/ethyl acetate gave an $R_f$ of 0.33 for the product; the starting material had an $R_f$ of 0.43. The crude product was dissolved in methylene chloride, treated with activated charcoal and the filtrate was concentrated to a small volume and chilled. The separated off-white crystals were filtered to afford 0.41 g (68%) of methyl 2-n-butyl-1-(2-chlorophenyl)methyl-5-phenyl-1H-benzimidazole-7-carboxylate; mp 103°-105° C.

(iii)2-n-butyl-1-(2-chlorophenyl)methyl-5-phenyl-1H-benzimidazole-7-carboxylic acid A mixture of methyl 2-n-butyl-1-(2-chlorophenyl)-methyl-5-phenyl-1H-benzimidazole-7-carboxylate (0.41 g, 0.95 mmol), ethanol (10 mL) and 10% sodium hydroxide solution (1 mL) was stirred for 18 hours as the starting ester slowly went into solution. Some solid was filtered and the filtrate was diluted with water (20 mL) and acidified to pH 3.4 with dilute hydrochloric acid. The precipitated solid was isolated (290 mg), dried and recrystallized from a small volume of toluene (after charcoal treatment) to provide a first crop of 165 mg (42%) of 2-n-butyl-1-(2 -chlorophenyl)methyl-5-phenyl-1H-benzimidazole-7-carboxylic acid; mp 236°-238° C.

Example 7

2-n-Butyl-6-chloro-1-(2-chlorophenyl)methyl-1H-benzimidazole-7-carboxylic Acid (i) 2,6-dichloro-3-nitrobenzoic acid The procedure described in K. Lehmstedt and K. Schrader, Chem. Berichte 70, 1526, (1937) was used. From 28.23 g (148 mmol) of 2,6-dichlorobenzoic acid, 75 mL of sulfuric acid, 6.75 mL of fuming nitric acid in 22.5 mL of sulfuric acid at 70°-90° C. was obtained 29.48 g of crude nitrated product. Crystallization from toluene afforded 14.92 g (43%) of 2,6-dichloro-3-nitrobenzoic acid; mp 133°-135° C.

(ii) 6-chloro-2-[(2-chlorophenyl)methyl]amino-3-nitrobenzoic acid

The procedure of Example 1 (ii) was followed using 10 g (42.4 mmol) of 2,6-dichloro-3-nitrobenzoic acid and proportional amounts of other reagents in place of 2,5-dibromo-3-nitrobenzoic acid, diluting with 10% aqueous hydrochloric acid, filtering off crystals to give the title compound as a crystalline solid (4.37 g, 30%); mp 151°-151.5° C.

(iii)2-n-butyl-6-chloro-1-(2-chlorophenyl)-methyl-1H-benzimidazole-7-carboxylic acid The procedure of Example 1 (iii-iv) was followed using 6-chloro-2-[(2-chlorophenyl)methyl]amino-3-nitro-benzoic acid in place of 5-bromo-2-[(2-chlorophenyl)methyl]amino-3-nitrobenzoic acid. The title compound was a white solid; mp 248.5°-250° C. (from methanol).

Example 8

2-n-Butyl-1-(2-chloro-6-fluorophenyl)methyl-1H-benzimidazole-7-carboxylic Acid

The procedure of Example 3 (i, ii-Method A) is followed using 2-chloro-6-fluorobenzylamine in place of 2-chlorobenzylamine to give the title compound.

Example 9

2-[2-n-Butyl-1-(2-chlorophenyl)methyl-1H-benzimidazol-7-yl]acetic acid (i) 2-n-butyl-1-(2-chlorophenyl)methyl-7-hydroxymethyl-1H-benzimidazole A suspension of 2-n-butyl-1-(2-chlorophenyl)methyl-1H-imidazole-7-carboxylic acid (Example 3) (9.06 g, 26.4 mmol) in dry tetrahydrofuran (950 mL) under an argon atmosphere was treated dropwise with a solution of diborane in tetrahydrofuran (105.2 mL of 1M diborane). The mixture was stirred at ambient temperature overnight. The reaction was cooled, treated with excess methanol continuously and the solvents were evaporated. The residue was dissolved in methylene chloride, and the solution was washed well with water, dried and concentrated. The crude product was chromatographed over 500 g of silica gel with a gradient of methanol in methylene chloride to give about 5 g of product. This was boiled in 10% hydrochloric acid (100 mL) and then chilled. The yellow crystals were filtered to provide 4.78 g of 2-n-butyl-1-(2-chlorophenyl)methyl-7-hydroxymethyl-1H-benzimidazole hydrochloride; mp 223°-233.5° C.

(ii) 2-n-butyl-7-chloromethyl-1-(2-chlorophenyl)-methyl-1H-benzimidazole

To a suspension of 2-n-butyl-1-(2-chlorophenyl)methyl-7-hydroxymethyl-1H-benzimidazole (1.01 g, 2.76 mmol) in methylene chloride (50 mL) was added thionyl chloride (0.61 mL). The resulting solution was stirred at ambient temperature for one hour, the solvent was evaporated, the residue triturated with toluene and then petroleum ether, and the white crystals (1.06 g) of 2-n-butyl-7-chloromethyl-1-(2-chlorophenyl)methyl-1H-benzimidazole were isolated and washed well with ether to give the title compound as the hydrochloride salt; mp 180°-184° C.

(iii) 2-n-butyl-1-(2-chlorophenyl)methyl-7-cyanomethyl-1H-benzimidazole

A mixture of 2-n-butyl-7-chloromethyl-1-(2-chlorophenyl)methyl-1H-benzimidazole, hydrochloride (1 g, 2.6 mmol) in dimethylsulfoxide (10 mL) was treated with sodium cyanide (153 mg, 3.12 mmol). The solid slowly went into solution, and after stirring for 3 hours at 25° C., the reaction was poured into water, some ammonium hydroxide solution was added and the resulting white precipitate was isolated to give 0.77 g of crude product; mp 122°-124° C. Crystallization from methylene chloride/hexane provided 0.68 g (84% of 2-n-butyl-1-(2-chlorophenyl)methyl-7-cyanomethyl-1H-benzimidazole; mp 124°-125° C.

(iv) 2-[2-n-butyl-1-(2-chlorophenyl)methyl-1H-benzimidazol-7-yl]acetic acid

A solution of 2-n-butyl-1-(2-chlorophenyl)methyl-7-cyanomethyl-1H-benzimidazole (0.26 g, 0.77 mL) in 10% aqueous hydrochloric acid solution was refluxed for 4 hours, ice was added and the pH was adjusted to 3.5 with 5% sodium carbonate solution. The precipitated solid was filtered to give 0.27 g of product; mp 212°-215° C. Crystallization from methanol provided 228 mg (83%) of 2-[2-n-butyl-1-(2-chlorophenyl)methyl-1H-benzimidazol-7-yl]acetic acid; mp 216°-217° C.

Example 10

3-[2-n-Butyl-1-{(2-chlorophenyl)-methyl}-1H-benzimidazol-7-yl]-2-(2-thienyl)methyl-2-propenoic Acid (i) 2-n-butyl-1-(2-chlorophenyl)methyl-1H-benzimidazole-7-carboxaldehyde A suspension of 2-n-butyl-1-(2-chlorophenyl)methyl-6-hydroxymethyl-1H-benzimidazole (1 g, 3.04 mmol, prepared in Example 9(i)), toluene (500 mL) and activated manganese dioxide (4 g) was refluxed with a Dean-Stark water separator for 4 hours. The mixture was filtered hot, concentrated and the crude product was treated with celite in methylene chloride to afford, after concentration, a residue that crystallized. Recrystallization from hexane gave 0.65 g (66%) of 2-n-butyl-1-{(2-chlorophenyl)methyl}-1H-benzimidazole-7-carboxaldehyde; mp 113.5°-115° C.

(ii) methyl 3-[2-n-butyl-1-{(2-chlorophenyl)methyl}-1H-benzimidazol-7-yl]-3-hydroxy-2-(2-thienyl)-methyl-propenoate A solution of n-butyl lithium (0.4 mL of 2.5M in hexane, 1 mmol) in dry tetrahydrofuran (5 mL) at −78° C. under argon was treated with diisopropylamine (108 mg, 1.06 mmol). This mixture was stirred 10 minutes at −78° C. and methyl 3-(2-thienyl)propanoate (156 mg, 0.92 mmol) was added in tetrahydrofuran. After being stirred an additional 30 minutes at −78° C., a solution of 2-n-butyl-1-(2-chlorophenyl)methyl-1H-benzimidazole-7-carboxaldehyde (200 mg, 0.61 mmol) in tetrahydrofuran (1.5 mL) was added. This mixture was stirred at −78° C. for 15 minutes and the reaction was quenched with saturated ammonium chloride. The product was extracted into ethyl acetate, washed with water, dried and concentrated product was flash chromatographed over silica gel with 5-10% of methanol in ethyl acetate to provide 0.17 g (56%) of methyl 3-[2-n-butyl-1-{(2-chlorophenyl)methyl}-1H-benzimidazol-7-yl]-3-hydroxy-2-(2-thienyl)methylpropanoate as an oil.

(iii) methyl-3-[2-n-butyl-1-{(2-chlorophenyl)methyl}-1H-benzimidazol-7-yl]-2-(2-thienyl)methyl-2-propenoate A solution of methyl 3-[2-n-butyl-1-{(2-chlorophenyl)-methyl}-1H-benzimidazol-7-yl]-3-hydroxy-2-(2-thienyl)-methylpropanoate (0.17 g, 0.34 mmol), methylene chloride (5 mL), 4-dimethylaminopyridine (15 mg) and acetic anhydride (0.32 mL, 3.4 mmol) was stirred for one hour, water (20 mL) was added and the mixture was stirred for 15 minutes. The organic layer was separated, washed with 5% sodium bicarbonate solution, dried with anhydrous magnesium sulfate, and concentrated to give 0.18 g of the acetate derivative. This intermediate was dissolved in toluene (12 mL) and refluxed to remove the residual water. The solution was stirred at 60° C. as 1,8-diazabicyclo[5.4.0]undec-7-ene (155 mg, 1.02 mmol) was added. The solution was stirred at 80° C. for 18 hours and then concentrated. The crude product was chromatographed on silica gel eluting with 2% methanol in methylene chloride to give 0.15 g of crystalline product. Crystallization from hexane gave methyl-3-[2-n-butyl-1-{(2-chlorophenyl)methyl-1H-benzimidazol-7-yl]-2-(2-thienyl)-methyl-2-propenoate; mp 129°-135° C.

(iv) 3-[2-n-butyl-1-{(2-chlorophenyl)methyl}-1H-benzimidazol-7-yl]-2-(2-thienyl)methyl-2-propenoic acid A solution of 0.15 g of the precursor methyl ester in ethanol (10 mL) and 10% sodium hydroxide solution (1 mL) was stirred overnight at 25° C. The alcohol was evaporated, water (10 mL) was added and the aqueous layer was extracted with ether. The aqueous layer was acidified (pH 3.5) and the product was isolated as a solid; mp 200°-202° C.

Example 11

2-n-Butyl-1-(4-carboxylphenyl)methyl-5-chloro-1H-benzimidazole-7-carboxylic Acid (i) 2-[4-carboxyphenyl)methyl]amino-5-chloro-3-nitrobenzoic acid A mixture of 2,5-dichloro-3-nitrobenzoic acid [K. Lehmstedt and K. Schrader, Berichte, 70, 1526 (1937)] (23.60 g, 100 mmol), powdered potassium carbonate (41.4 g, 300 mmol) and 4-(aminomethyl)benzoic acid (400 mmol, 60.04 g) in 250 mL of methanol was stirred at reflux under argon. After 16 hours at reflux, the reaction mixture was poured into 650 mL of 10% hydrochloric acid solution, and the solid which formed was filtered. The collected solid was triturated with ethyl acetate to remove the product. The ethyl acetate solution was concentrated in vacuo to give 20.15 g (57.5%) of a yellow-orange solid.

(ii) 2-[4-carboxyphenyl)methyl]-N-valeryl]amino-5-chloro-3-nitrobenzoic acid

The procedure of Example 1(iii) was followed using 2-[(4-carboxyphenyl)methyl]amino-5-chloro-3-nitrobenzoic acid (6.50 g, 10.54 mmol) in place of 5-bromo-2-[(2-chlorophenyl)methyl]amino-3-nitrobenzoic acid to give 6.66 g, (82.6%) of 2-[(4-carboxyphenyl)methyl-N-valeryl]amino-6-chloro-3-nitrobenzoic acid.

(iii) 2-n-butyl-1-(2-carboxyphenyl)methyl-5-chloro-1H-benzimidazole-7-carboxylic acid The procedure of Example 1(iv) was followed using 2-[(4-carboxyphenyl)methyl-N-valeryl]amino-5-chloro-3-nitrobenzoic acid (5.34 g, 13.43 mmol) in place of 5-bromo-2-[(2 -chlorophenyl)methyl-N-valeryl]amino-3-nitrobenzoic acid to give 3.19 g (64%) of a product which was recrystallized from methanol; mp 275°–275.5° C.

Example 12

2-n-Butyl-1-(2-chlorophenyl)methyl-1H-benzimidazole-5,7-dicarboxylic Acid

The methyl ester of 5-bromo-2-n-butyl-1-(2-chlorophenyl)methyl-1H-benzimidazole-7-carboxylic acid (prepared in Example 1) was formed by the action of methanol-hydrochloric acid. This ester (517 mg, 1.19 mmol), calcium formate (93 mg, 0.71 mmol), triphenylphosphine (93 mg, 0.35 mmol) and palladium chloride (11 mg, 0.06 mmol) were placed under an argon atmosphere and diluted with 4.0 mL of benzene and 4.0 mL of dimethylformamide. The argon atmosphere was replaced by carbon monoxide at 50 psig. The sealed vessel was heated for 65 hours at 120° C.

The reaction mixture was filtered and the filtrate was concentrated in vacuo. The resulting oil was triturated with ethyl acetate to give a solid, which was dissolved in 10% sodium hydroxide solution. The basic extract was washed with diethyl ether and then made acidic with 10% hydrochloric acid solution to give 0.31 g of a solid.

This half acid-half ester compound was converted to the corresponding diacid by the action of methanol-hydrochloric acid and chromatography on silica gel gave 90 mg of solid product (mp 99°–101° C). Hydrolysis of the ester groups was carried out with 3.0 mL of ethanol containing 0.3 mL of 10% sodium hydroxide solution. After removal of the ethanol, the basic solution was acidified and a solid formed. The solid was collected and dried to give 77 mg of the title compound as a monohydrate; mp 299°–301° C.

Alternatively, the sodium salt of the acid is isolated directly from the reaction mixture, prior to neutralization. The crude basic reaction solution is applied to a reverse-phase flash column equilibrated with water. The inorganics are washed from the column equilibrated with water (3 void volumes) and then the product is eluted with a 50:50 mixture of acetonitrile in water. The acetonitrile is removed in vacuo and then the desired sodium salt is obtained after lyophilization.

Example 13

2-n-Butyl-1-(2-chlorophenyl)methyl-5,6-dichloro-1H-benzimidazole-7-carboxylic Acid

(i) 3-nitro-2,5,6-trichlorobenzoic acid 2,3,6-Trichlorobenzoic acid (20.84 g, 92.4 mmol, prepared by the method of M. T. Goebel, U.S. Pat. No. 3,391,185, E.I. DuPont, Jul. 2, 1968) was stirred at 40°–45° C. in 89.1 mL of concentrated sulfuric acid. A solution containing 23.2 g of concentrated sulfuric acid and 23.2 g of fuming nitric acid was added at a rate so to maintain the temperature between 40°–45° C. An additional 20 mL of concentrated sulfuric acid was added. The reaction mixture was stirred at 43° C. for 1.5 hours and then poured over ice water. The resulting crystals were filtered and recrystallized from toluene-hexane to give 23.40 g (94%) of product; mp 149°–151° C.

(ii) 2-[(2-chlorophenyl)methyl]amino-5,6-dichloro-3-nitrobenzoic acid

To a stirred solution of 3-nitro-2,5,6-trichlorobenzoic acid (37.1 mmol, 10.0 g) in 150 mL of toluene, was added 2-chlorobenzylamine (81.6 mmol, 11.56 g). The reaction mixture was refluxed overnight, poured into dilute hydrochloric acid and vigorously stirred. The resulting solid was filtered. The product was dissolved in toluene and then precipitated with diethyl ether. Recrystallization of the product from methanol gave 3.4 g of 2-[2-chlorophenyl)methyl]amino-5,6-dichloro-3-nitrobenzoic acid; mp 168.5°–171° C.

(iii) 2-[(2-chlorophenyl)methyl-N-valeryl]amino-5,6-dichloro-3-nitrobenzoic acid The procedure of Example 1(iii) was followed using 2-[(2-chlorophenyl)methyl]amino-5,6-dichloro-3-nitrobenzoic acid (4.11 g, 10.94 mmol) in place of 5-bromo-2-[(2-chlorophenyl)methyl]-amino-3-nitrobenzoic acid to give 3.73 (84%) of 2-[(2-chlorophenyl)-methyl-2-N-valeryl]amino-5,6-dichloro-3-nitrobenzoic acid; mp 202°–203° C.

(iv) 2-n-butyl-1-(2-chlorophenyl)methyl-5,6-dichloro-1H-benzimidazole-7-carboxylic acid The procedure of Example 1(iv) was followed using 2-[(2-chlorophenyl)methyl-N-valeryl]amino-5,6-dichloro-3-nitrobenzoic acid (3.66 g, 7.96 mmol) in place of 5-bromo-2-[(2-chlorophenyl)methyl-N-valeryl]amino-3-nitrobenzoic acid to give 2-n-butyl-1-(2-chlorophenyl)methyl-5,6-dichloro-1H-benzimidazole-7-carboxylic acid; mp 240°–240.5° C.

Example 14

L-α-Amino-N-(2-n-butyl-1H-benzimidazole-1-propanoyl)-2-(2-thienyl)methylpropanoic Acid

(i) 3-(2-n-butyl-1H-benzimidazole-1-yl)propanoic acid 2-n-Butyl benzimidazole (5.00 g, 2.87 mmol) was heated under argon in an oil bath at 150° C. To the molten material was added acrylic acid (3.58 mmol, 2.58 g). After 2 hours at 150° C., the reaction mixture had solidified. The solid was cooled and triturated with methylene chloride (2:1) to give 3.44 g of a solid. The solid was diluted with 5% sodium hydroxide solution, filtered, and made acidic to pH 3.22. The resulting solid was filtered and then recrystallized from methanol to give 3.09 g (44%) of 3-(2-n-butyl-1H-benzimidazol-1-yl)-propanoic acid; mp 177°–177.5° C.

(ii) L-α-amino-N-(2-n-butyl-1H-benzimidazole-1-propanoyl)-2-(2-thienyl)methylpropanoic acid, methyl ester 3-(2-n-Butyl-1H-benzimidazol-1-yl)propanoic acid (500 mg, 2.03 mmol) was mixed with N-hydroxysuccinimide (257 mg, 2.28 mmol) and placed under an argon atmosphere. To this was added 10 mL of methylene chloride. Dicyclohexylcarbodiimide (460 mg) dissolved in 7 mL of methylene chloride was added dropwise to this mixture over a period of 20 minutes and then stirred for 30 minutes. Thienyl alanine methyl ester hydrochloride (518 mg, 2.23 mmol) was added in a single portion, followed immediately by triethylamine (4.06 mmol, 410 mg). The reaction mixture was stirred at ambient temperature overnight and then it was filtered. The filtrate was concentrated to a semi-solid and chromatographed on silica gel with 0.5% methanol in chloroform to give a solid. This product was recrystallized from methylene chloride/hexane to give 740 mg (88%) of L-α-amino-N-(2-n-butyl-1H-benzimidazole-1-propanoyl)-2-(2-thienyl)methylpropanoic acid, methyl ester; mp 128°-128.5° C., $[\alpha]_D^{25} = -10.35$ (c=1, methanol).

(iii) L-α-amino-N-(2-n-butyl-1H-benzimidazole-1-propanoyl)-2-(2-thienyl)methylpropanoic acid L-α-amino-N-(2-n-butyl-1H-benzimidazole-1-propanoyl)-2-(2-thienyl)methylpropanoic acid, methyl ester (480 mg, 1.16 mmol) was stirred under argon in a mixture of 1.2 mL of 10% sodium hydroxide solution and 1.2 mL ethanol at ambient temperature overnight. The ethanol was boiled off and the aqueous layer was diluted with 5 mL of water. The aqueous extract was washed with diethyl ether and then it was made acidic with 10% hydrochloric acid (pH 3.34). The isolated crystals (0.34 g, 73%) were hygroscopic; mp 220°-220.5° C., $[\alpha]_D^{25} = +1.80$ (c=1, dimethylformamide).

Example 15

L-α-Amino-N-(2-n-butyl-1H-benzimidazole-1-acetoyl)-2-(2-thienyl)methylpropionic Acid (i) 2-n-butyl-1H-benzimidazole-1-acetic acid 2-n-Butyl benzimidazole (3.00 g, 17.22 mmol) was mixed with powdered potassium carbonate (2.62 g, 19 mmol) and diluted with 25 mL dimethylformamide. To this was added ethyl bromoacetate (18.94 mmol). The reaction mixture was stirred at ambient temperature overnight and poured into 150 mL of water. The resulting crystals were filtered, and recrystallized from hexane to give 2.26 g (50%) of a solid; mp 70°-71° C.

The ester compound prepared above (1.96 g, 7.53 mmol) was stirred under argon in a mixture of 50 mL of ethanol and 5 mL of 10% sodium hydroxide solution for 2 hours. The reaction mixture was filtered and then the filtrate was concentrated in vacuo. The residue was dissolved in water, and the pH was adjusted to pH 3.37 with 10% hydrochloric acid solution to give 1.59 g (91%) crystals; mp 184°-184.5° C.

(ii) L-α-amino-N-(2-n-butyl-1H-benzimidazole-1-acetoyl)-2-(2-thienyl)methylpropionic acid, methyl ester The title compound was prepared following the procedure of Example 14(ii) using 2-n-butyl-1H-benzimidazole-1-acetic acid (0.26 g, 1.12 mmol) in place of 3-(2-n-butyl-1H-benzimidazol-1-yl)propanoic acid to give 0.17 g (38%) of L-α-amino-N-(2-n-butyl-1H-benzimidazole-1-acetoyl)-2-(2-thienyl)methylpropionic acid, methyl ester; mp 125°-126.5° C.

(iii) L-α-amino-N-(2-n-butyl-1H-benzimidazol-1-acetoyl)-2-(2-thienyl)methylpropionic acid The ester compound prepared above (0.16 g, 0.40 mmol) was stirred as a suspension in 4.0 ml of ethanol containing 0.4 mL 10% sodium hydroxide solution under argon for 16 hours. The ethanol was removed, and the solid was stirred in 20 mL of water, filtered, and made acidic to pH 3.72 with 10% hydrochloric acid solution. The resulting crystals were recrystallized from methanol to give 0.092 g (60%) L-α-amino-N-(2-n-butyl-1H-benzimidazole-1-acetoyl)-2-(2-thienyl)methylpropionic acid; mp 277°-279° C., $[\alpha]_D^{25} = +18.06$ (c=0.49, dimethylformamide).

Example 16

L-α-Amino-N-[[2-n-butyl-1[(2-chlorophenyl)methyl]-1H-benzimidazole-7-acetoyl]-2-(2-thienyl)methylpropionic Acid (i) L-α-amino-N-[[2-n-butyl-1-[(2-chlorophenyl)methyl]-1H-benzimidazole-7-acetoyl]-2-(2-thienyl)methylpropionic acid, methyl ester The title compound was prepared following the procedure of Example 14(ii) using 2-n-butyl-1-(2-chlorophenyl)methyl-1H-benzimidazole-7-acetic acid (150 mg, 0.42 mmol, prepared in Example 9) in place of 3-(2-n-butyl-1H-benzimidazol-1-yl)propanoic acid to give 0.19 g (86%) of L-α-amino-N-[[2-n-butyl-1-[(2-chlorophenyl)methyl]-1H-benzimidazole-7-acetoyl]-2-(2-thienyl)methylpropionic acid, methyl ester; mp 117°-118° C.

(ii) L-α-amino-N-[[2-n-butyl-1-[(2-chlorophenyl)methyl]-1H-benzimidazole-7-acetoyl]-2-(2-thienyl)methylpropionic acid The title compound was prepared following the procedure of Example 15(iii) using L-α-amino-N-[[2-n-butyl-1-[(2 -chlorophenyl)methyl]-1H-benzimidazole-7-acetoyl]-2-(2-thienyl)methylpropionic acid, methyl ester (0.19 g, 0.36 mmol) in place of L-α-amino-N-(2-n-butyl-1H-benzimidazole-1-acetoyl)-2-(2-thienyl)methylpropionic acid, methyl ester to give 0.11 g (58% of L-α-amino-N-[2-n-butyl-1-(2-chlorophenyl)methyl-1H-benzimidazole-7-acetoyl]-2-(2-thienyl)methylpropionic acid; mp 202°-204° C. (from methanol, $[\alpha]_D^{25} = +15.0°$ (c=1, dimethylformamide)).

Example 17

L-α-Amino-N-[[2-n-butyl-1-(2-chlorophenyl)methyl-1H-benzimidazole-7-ethyl]-2-(2-thienyl)methylpropionic Acid 2-[2-n-Butyl-1-(2-chlorophenyl)methyl-1H-benzimidazole-7-yl]acetic acid (1.10 g, mmol, prepared in Example 9) was reduced with diborane in tetrahydrofuran following the procedure of Example 9(i) to give 1.09 g of a solid, which was recrystallized from methylene chloride/hexane to give 0.84 g of 2-n-butyl-1-(2-chlorophenyl)methyl-7-hydroxyethyl-1H-benzimidazole; mp 130.5°-132° C.

This alcohol (0.546 g, 1.59 mmol) was treated following the procedure of Example 9(ii) to give 540 mg of 2-n-butyl-7-chloroethyl-1-(2-chlorophenyl)methyl-1H-benzimidazole as an oil.

To a solution of (2-thienyl)alanine methyl ester hydrochloride in dry dimethylformamide was added triethylamine, and then a solution of 2-n-butyl-7-chloroethyl-1-(2-chlorophenyl)methyl-1H-benzimidazole in dimethylformamide. The mixture was heated on a steam bath for 3 hours under argon, poured into water and the product was extracted into ethyl acetate. The water-washed, dried, concentrated product was flash chromatographed over silica gel to give L-α-amino-N-[(2-n-butyl-1-(2-chlorophenyl)-methyl-1H-benzimidazole-7-ethyl]-2-(2-thienyl)methylpropionic acid.

The ester (220 mg, 0.43 mmol) was subjected to acid hydrolysis (4.0 mL, 6N aqueous hydrochloric acid solution, 25° C.) to give 94 mg (44%) of the title compound; mp 178°-179° C., $[\alpha]_D^{25} = -4.80°$ C. (c=0.5, dimethylformamide).

Example 18

1-(2-Chlorophenyl)methyl-2-heptafluoropropyl-1H-benzimidazole-7-carboxylic Acid

3-Amino-2-[(2-chlorophenyl)methyl]aminobenzoic acid (1.00 g, 3.69 mmol, prepared in Example 3, (i) and (ii), method B) was refluxed under argon with 7.96 mmol of heptafluorobutyric anhydride for 16 hours. To the reaction mixture was added 6.6 mL heptafluorobutyryl chloride and 4.0 mL of concentrated hydrochloric acid. This mixture was heated for 2 hours at 102° C. The organic phase was separated and concentrated to an oil. The residue was dissolved in diethyl ether, filtered, and allowed to stand. Crystals formed which were recrystallized from hot hexane to give 0.55 g (33.6%) of the title compound; mp 213°–213.5° C.

Example 19

2-n-Butyl-5-chloro-1-(2-chlorophenyl)methyl-1H-benzimidazole-7-carboxylic Acid 2-n-Butyl-5-chloro-3-nitrobenzoic acid was prepared by the method of R. K. Bentley and F. G. Hollinian, J. Chem. Soc., (c), 2447 (1970); mp 218.5°–220° C.

2-Bromo-5-chloro-3-nitrobenzoic acid (2.30 g, 10 mmol) was refluxed with 2-chlorobenzyl amine (20 mmol, 2.82 g) overnight. The reaction mixture was then poured into 10% aqueous hydrochloric acid solution and the resulting solid was collected. Crystallization from aqueous methanol gave 1.81 g (53%) of 5-chloro[(2-chlorophenyl)methyl]amino-3-nitrobenzoic acid; mp 159.5°–161° C.

The procedure of Example 1(iii and iv) was followed using 5-chloro-2-[(2-chlorophenyl)methyl]amino-3-nitrobenzoic acid (1.50 g, 4.40 mmol) in place of 5-bromo-2-[(2-chlorophenyl)methyl]amino-3-nitrobenzoic acid to give 1.48 g (89.3%) of the title compound, which was recrystallized from methanol; mp 261°–262° C.

Example 20

2-n-Butyl-1-(4-carboxyphenyl)-5-chloro-1H-benzimidazole-7-carboxylic Acid (i) 5-chloro-2-(4-carboxyphenyl)amino-3-nitrobenzoic acid A mixture of 2,5-dicho-3-nitrobenzoic acid (1.0, 4.23 mmol), methyl-4-aminobenzoate (3.22 g, 21.3 mmol), and 50 mg of powdered copper under argon were heated in an oil bath at 140° C. for 30 minutes. The reaction mixture was then sonicated with 10% aqueous hydrochloric acid solution and the resulting crystals were collected. The solid was stirred with 10% aqueous sodium hydroxide solution for 15 minutes and then acidified with concentrated hydrochloric acid to give 0.79 g (53.3%) of the title compound mp 264°–266° C.

(ii) 2-n-butyl-1-(4-carbomethoxyphenyl)amino-3-nitrobenzoic acid

The procedure of Example 1 (iii-iv) was followed using 5-chloro-2-(4-carbomethoxyphenyl)amino-3-nitrobenzoic acid in place of 5-bromo-2-[(2-chlorophenyl)methyl]amino-3-nitrobenzoic acid to give the title compound; mp 308°–309° C.(d).

Example 21

1-(4-carboxyphenyl)methyl-6-chloro-1H-benzimidazole-7-carboxylic Acid

A solution of 3-amino-2-[(4-carboxyphenyl)methyl]amino-6-chlorobenzoic acid (80 mg, 0.24 mmol, prepared as in Example 2 (i-ii)) in 0.5 ml of 98% formic acid was refluxed under argon for 2.5 hours. The reaction mixture was diluted with water and the resulting solid was collected to give 80 mg (100%) of the title compound; mp 291°–292° C.

Example 22

2-n-Butyl-1-(4-carboxylphenyl)ethyl-5-chloro-1H-benzimidazole-7-carboxylic Acid (i) 5-chloro-2-[(4-carboxyphenyl)ethyl]amino-3-nitrobenzoic acid A mixture of 2,5-dichloro-3-nitrobenzoic acid (23.6 g, 100 mmol), powdered potassium carbonate (41.1 g, 300 mmol), and 4-(aminoethyl)benzoic acid (60.04 g, 400 mmol) in 250 ml of methanol was refluxed under argon for 18 hours. The reaction mixture was poured into 650 ml of 10% aqueous hydrochloric acid solution. The solid was collected and triturated with ethyl acetate. The ethyl acetate extract was decanted, dried with magnesium sulfate and concentrated in vacuo to give 20.15 g (57.5%) of the title compound; mp 255°–257° C.

(ii) 2-n-butyl-1-(4-carboxyphenyl)ethyl-5-chloro-1H-benzimidazole-7-carboxylic acid The procedure of Example 2 (ii-iv) was followed using 5-chloro-2-[(4-carboxyphenyl)ethyl]amino-3-nitrobenoic acid in place of 3-[(2-chlorophenyl)methyl]amino-4-nitrobenzoic acid to give the title compound; mp 312°–315° C.

Example 23

2-n-butyl-1-(4-carboxyphenyl)methyl-5-chloro-4-methyl-1H-benzimidazole-7-carboxylic Acid The procedure of Example 23 was followed except ethanol was used in place of methanol and powdered copper was added to the reaction mixture described in Example 23 (i) to give the title compound; mp 293°–294° C.

Example 24

The following compounds are prepared by the procedures hereinbefore described:

2-n-butyl-1-(3-chloro-4-carboxyphenyl)methyl-5-chloro-1H-benzimidazole-7-carboxylic acid;

2-n-butyl-1-(2,3-dichloro-4-carboxyphenyl)methyl-6-chloro-1H-benzimidazole-7-carboxylic acid, 2-n-butyl-1-(2-chloro-4-carboxyphenyl)methyl-6-chloro-1H-benzimidazole-7-carboxylic acid, ethyl ester;

2-n-butyl-1-(2-chlorophenyl)methyl-4,5-dichloro-1H-benzimidazole-7-carboxylic acid;

2-n-butyl-1-(4-carboxyphenyl)methyl-5-bromo-1H-benzimidazole-7-carboxylic acid, ethyl ester;

2-(1-butenyl)-1-(4-carboxyphenyl)methyl-6-chloro-1H-benzimidazole-7-carboxylic acid;

2-n-butyl-1-(3-trifluoromethyl-4-carboxyphenyl)-methyl-5-chloro-1H-benzimidazole-7-carboxylic acid;

2-n-propyl-1-(3-chloro-4-carboxyphenyl)methyl-5-chloro-1H-benzimidazole-7-carboxylic acid; and 2-n-hexyl-1-(2-chloro-4-carboxyphenyl)methyl-5-chloro-1H-benzimidazole-7-carboxylic acid.

Example 25

An oral dosage form for administering orally active Formula (I) compounds is produced by screening, mixing and filling into hard gelatin capsules the ingredients in proportions, for example, as shown below.

| Ingredients | Amounts |
|---|---|
| 2-n-butyl-6-chloro-1-(2-chlorophenyl)methyl-1H-benzimidazole-7-carboxylic acid | 100 mg |
| magnesium stearate | 10 mg |
| lactose | 100 mg |

Example 26

The sucrose, calcium sulfate dihydrate and orally active Formula (I) compounds are mixed and granulated with a 10% gelatin solution. The wet granules are screened, dried, mixed with the starch, talc and stearic acid, screened and compressed into a tablet.

| Ingredients | Amounts |
|---|---|
| 5-bromo-2-n-butyl-1-(2-chlorophenyl)-methyl-1H-benzimidazole-7-carboxylic acid | 75 mg |
| calcium sulfate dihydrate | 100 mg |
| sucrose | 15 mg |
| starch | 8 mg |
| talc | 4 mg |
| stearic acid | 2 mg |

Example 27

2-n-Butyl-1-(2-chlorophenyl)methyl-7-(1H-tetrazol-5-yl)-1H-benzimidazole, 50 mg, is dispersed in 25 ml of normal saline to prepare an injectable preparation.

Example 28

A topical ophthalmological solution for administering Formula (I) compounds is produced by mixing under sterile conditions the ingredients in proportions, for example, as shown below.

| Ingredients | Amounts (mg/ml) |
|---|---|
| 2-n-butyl-1-(2-chlorophenyl)methyl-1H-benzimidazole-5,7-dicarboxylic acid | 1.0 |
| dibasic sodium phosphate | 10.4 |
| monobasic sodium phosphate | 2.4 |
| chlorobutanol | 5.0 |
| hydroxypropanol methylcellulose | 5.0 |
| sterile water | q.s. ad 1.0 ml |
| 1.0N sodium hydroxide | q.s. ad pH 7.4 |

It is to be understood that the invention is not limited to the embodiments illustrated hereabove and the right to the illustrated embodiments and all modifications coming within the scope of the following claims is reserved.

What is claimed is:

1. A compound of the formula:

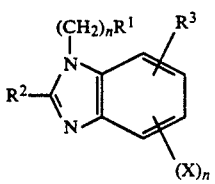

in which:

$R^1$ is —C(O)NH—CH(Y)—$(CH_2)_n$-aryl, —C(O)NH—CH(Y)—$(CH_2)_n$-heteroaryl, or phenyl unsubstituted or substituted by one to three substituents selected from Cl, Br, F, I, $C_{1-6}$alkyl, $C_{1-6}$alkoxy, OH, CN, $NO_2$, $CO_2R^4$, tetrazol-5-yl, $CONR^4R^4$, $SO_3H$, $C_mF_{2m+1}$, $SC_{1-6}$alkyl, or $SO_2C_{1-6}$alkyl;

$R^2$ is hydrogen, $C_{2-10}$alkyl, $C_{3-10}$alkenyl, $C_{3-6}$-cycloalkyl, $C_mF_{2m+1}$, or $(CH_2)_{0-8}$phenyl unsubstituted or substituted by one to three substituents selected from $C_{1-6}$alkyl, $C_{1-6}$alkoxy, Cl, Br, F, I, OH, $NO_2$, $C_mF_{2m+1}$, $CO_2R^4$, or $NR^4R^4$;

$R^3$ is —$(CH_2)_n$—Y, —CH=CY—$(CH_2)_n$-aryl, —CH=CY—$(CH_2)_n$-heteroaryl, —$(CH_2)_n$—C(O)—NH—CH(Y)—$(CH_2)_n$-aryl, —$(CH_2)_n$—C(O)—NH—CH(Y)—$(CH_2)_n$heteroaryl, —$(CH_2)_m$—NH—CH(Y)—$(CH_2)_n$-aryl or —$(CH_2)_m$—NH—CH(Y)—$(CH_2)_n$-heteroaryl, when $R^1$ is an optionally substituted phenyl group; or H when $R^1$ is —C(O)NH—CH(Y)—$(CH_2)_n$-aryl or —C(O)NH—CH(Y)—$(CH_2)_n$-heteroaryl;

Y is $CO_2R^4$ or tetrazol-5-yl;

X is Cl, Br, F, I, $C_mF_{2m+1}$, $C_{1-6}$alkyl, $C_{1-6}$alkoxy, OH, O-phenyl, $CO_2R^4$, tetrazol-5-yl, CN, or $(CH_2)_{0-4}$phenyl unsubstituted or substituted by Cl, Br, F, I, $C_{1-6}$alkyl, $C_{1-6}$alkoxy, OH, $C_mF_{2m+1}$, CN, $CO_2R^4$, $NO_2$, or $NR^4R^4$;

aryl is phenyl, biphenyl, or naphthyl wherein each aryl group is unsubstituted or substituted by $C_{1-6}$alkyl, $C_{1-6}$alkoxy, Cl, Br, F, I, OH, $NO_2$, $CF_3$, $CO_2R^4$, or $NR^4R^4$;

heteroaryl is 2- or 3-thienyl, 2-, or 3-furanyl, 2-, 3-, or 4- pyridyl, pyrimidyl, imidazolyl, thiazolyl, triazolyl, or tetrazolyl wherein each heteroaryl group is unsubstituted or substituted by $C_{1-6}$alkyl, $C_{1-6}$alkoxy, Cl, Br, F, I, OH, $NO_2$, $CF_3$, $CO_2R^4$, or $NR^4R^4$;

each m independently is 1–3;

each n independently is 0–2; and each $R^4$ independently is H or $C_{1-6}$alkyl; or a pharmaceutically acceptable salt thereof.

2. A compound of claim 1 in which:

$R^1$ is —C(O)NH—CH(Y)—$(CH_2)_n$-2-thienyl or phenyl unsubstituted or substituted by one to three substituents selected from chloro, fluoro, nitro, methyl, cyano, carbomoyl, trifluoromethyl, carboxy, carbo$C_{1-2}$alkoxy, tetrazol-5-yl, methoxy, or hydroxy;

$R^2$ is hydrogen, $C_{2-8}$alkyl, or $C_mF_{2m+1}$;

$R^3$ is —$(CH_2)_n$—Y—, —CH=CY—$(CH_2)$-2-thienyl, —$(CH_2)_n$—C(O)—NH—CH(Y)—$(CH_2)_n$-2-thienyl, or —$(CH_2)_m$—NH—CH(Y)—$(CH_2)_n$-2-thienyl, when $R^1$ is an optionally substituted phenyl group; or H when $R^1$ is —C(O)NH—CH(Y)—$(CH_2)_n$-2-thienyl; and X is absent or present as $CO_2H$, tetrazol-5-yl, Cl, Br, F, $CF_3$, $CH_3$, or $(CH_2)_{0-2}$phenyl taken once or twice; or a pharmaceutically acceptable salt thereof.

3. A compound of claim 2 which is 2-n-butyl-1-(2-chlorophenyl)methyl-1H-benzimidazole-7-carboxylic acid or a pharmaceutically acceptable salt thereof.

4. A compound of claim 2 which is 5-bromo-2-n-butyl-1-(2-chlorophenyl)methyl-1H-benzimidazole-7-carboxylic acid or a pharmaceutically acceptable salt thereof.

5. A compound of claim 2 which is 2-n-butyl-1-(4-carboxyphenyl)methyl-5-chloro-1H-benzimidazole-7-carboxylic acid or a pharmaceutically acceptable salt thereof.

6. A compound of claim 2 which is:
2-n-butyl-1-(2-chlorophenyl)methyl-1H-benzimidazole-6-carboxylic acid;
2-n-butyl-5-phenyl-1-(2-chlorophenyl)methyl-1H-benzimidazole-7-carboxylic acid;
2-n-butyl-1-(2-chlorophenyl)methyl-7-(1H-tetrazol-5-yl)-1H-benzimidazole;
2-n-butyl-1-(2-chlorophenyl)methyl-1H-benzimidazole-5,7-dicarboxylic acid;
3-[2-n-butyl-1-(2-chlorophenyl)methyl-1H-benzimidazol-7-yl]-2-(2-thienyl)methyl-2-propenoic acid;
2-n-butyl-5,6-dichloro-1-(2-chlorophenyl)methyl-1H-benzimidazole-7-carboxylic acid;
2-[2-n-butyl-1-(2-chlorophenyl)methyl-1H-benzimidazol-7-yl]acetic acid;
L-α-amino-N-[2-n-butyl-1-(2-chlorophenyl)methyl-1H-benzimidazole-7-ethyl]-2-(2-thienyl)methylpropionic acid;
1-(2-chlorophenyl)methyl-2-heptafluoropropyl-1H-benzimidazole-6-carboxylic acid;
L-α-amino-N-(2-n-butyl-1H-benzimidazole-1-propanoyl)-2-(2-thienyl)methylpropanoic acid;
L-α-amino-N-(2-n-butyl-1H-benzimidazole-1-acetoyl)-2-(2-thienyl)methylpropionic acid;
L-α-N-[2-n-butyl-1-(2-chlorophenyl)methyl-1H-benzimidazole-7-acetoyl]-2-(2-thienyl)methylpropionic acid;
methyl L-α-amino-N-(2-n-butyl-1H-benzimidazole-1-propanoyl)-2-(2-thienyl)methylpropanoate;
2-n-butyl-6-chloro-1-(2-chlorophenyl)methyl-1H-benzimidazole-7-carboxylic acid;
2-n-butyl-1-(4-carboxyphenyl)-5-chloro-1H-benzimidazole-7-carboxylic acid;
1-(4-carboxypenyl)methyl-6-chloro-1H-benzimidazole-7-carboxylic acid;
2-n-butyl-1-(4-carboxyphenyl)ethyl-5-chloro-1H-benzimidazole-7-carboxylic acid;
2-n-butyl-1-(4-carboxyphenyl)methyl-5-chloro-4-methyl-1H-benzimidazole-7-carboxylic acid; or
2-n-butyl-5-chloro-1-(2-chlorophenyl)methyl-1H-benzimidazole-7-carboxylic acid; or a pharmaceutically acceptable salt thereof.

7. A pharmaceutical composition comprising a compound of claim 1 and suitable pharmaceutical carrier.

8. A pharmaceutical composition of claim 7 wherein the compound is 2-n-butyl-1-(2-chlorophenyl)methyl-1H-benzimidazole-7-carboxylic acid.

9. A pharmaceutical composition of claim 7, wherein the compound is 5-bromo-2-n-butyl-1-(2-chlorophenyl)-methyl-1H-benzimidazole-7-carboxylic acid.

10. A pharmaceutical composition of claim 7 wherein the compound is 2-n-butyl-1-(4-carboxyphenyl)methyl-5-chloro-1H-benzimidazole-7-carboxylic acid.

11. A pharmaceutical composition of claim 7 wherein the compound is:
2-n-butyl-1-(2-chlorophenyl)methyl-1H-benzimidazole-6-carboxylic acid;
2-n-butyl-5-phenyl-1-(2-chlorophenyl)methyl-1H-benzimidazole-7-carboxylic acid;
2-n-butyl-1-(2-chlorophenyl)methyl-7-(1H-tetrazol-5-yl)-1H-benzimidazole;
2-n-butyl-1-1(2-chlorophenyl)methyl-1H-benzimidazole-5,7-dicarboxylic acid;
3-[2-n-butyl-1-(2-chlorophenyl)methyl-1H-benzimidazol-7-yl]-2-(2-thienyl)methylmethyl-2-propenoic acid;
2-n-butyl-5,6-dichloro-1-(2-chlorophenyl)methyl-1H-benzimidazole-7-carboxylic acid;
2-[2-n-butyl-1-(2-chlorophenyl)methyl-1H-benzimidazol-7-yl]acetic acid;
L-α-amino-N-[2-n-butyl-1-(2-chlorophenyl)methyl-1H-benzimidazole-7-ethyl]-2-(2-thienyl)methylpropionic acid;
1-(2-chlorophenyl)methyl-2-heptafluoropropyl-1H-benzimidazole-6-carboxylic acid;
L-α-amino-N-(2-n-butyl-1H-benzimidazole-1-propanoyl)-2-(2-thienyl)methylpropanoic acid;
L-α-amino-N-(2-n-butyl-1H-benzimidazole-1-acetoyl)-2-(2-thienyl)methylpropionic acid;
L-α-N-[2-n-butyl-1-(2-chlorophenyl)methyl-1H-benzimidazole-7-acetoyl]-2-(2-thienyl)methylpropionic acid;
methyl L-α-amino-N-(2-n-butyl-1H-benzimidazole-1-propanoyl)-2-(2-thienyl)methylpropanoate;
2-n-butyl-6-chloro-1-(2-chlorophenyl)methyl-1H-benzimidazole-7-carboxylic acid;
2-n-butyl-1-(4-carboxyphenyl)-5-chloro-1H-benzimidazole-7-carboxylic acid;
1-(4-carboxyphenyl)methyl-6-chloro-1H-benzimidazole-7-carboxylic acid;
2-n-butyl-1-(4-carboxyphenyl)ethyl-5-chloro-1H-benzimidazole-7-carboxylic acid;
2-n-butyl-1-(4-carboxyphenyl)methyl-5-chloro-5-methyl-1H-benzimidazole-7-carboxylic acid; or
2-n-butyl-5-chloro-1-(2-chlorophenyl)methyl-1H-benzimidazole-7-carboxylic acid.

12. A method of antagonizing angiotensin II receptors in mammals which comprises administering to a subject in need thereof an effective amount of a compound of claim 1.

13. A method of claim 12 wherein the compound is 2-n-butyl-1-(2-chlorophenyl)methyl-1H-benzimidazole-7-carboxylic acid.

14. A method of claim 12 wherein the compound is 5-bromo-2-n-butyl-1-(2-chlorophenyl)methyl-1H-benzimidazole-7-carboxylic acid.

15. A method of claim 12 wherein the compound is 2-n-butyl-1-(4-carboxyphenyl)methyl-5-chloro-1H-benzimidazole-6-carboxylic acid.

16. A method of claim 12 wherein the compound is:
2-n-butyl-1-(2-chloropheny)methyl-1H-benzimidazole-6-carboxylic acid;
2-n-butyl-5-phenyl-1-(2-chlorophenyl)methyl-1H-benzimidazole-7-carboxylic acid;
2-n-butyl-1-(2-chlorophenyl)methyl-7-(1H-tetrazol-5-yl)-1H-benzimidazole;
2-n-butyl-1-1(2-chlorophenyl)methyl-1H-benzimidazole-5,7-dicarboxylic acid;
3-[2-n-butyl-1-(2-chlorophenyl)methyl-1H-benzimidazol-7-yl]-2-(2-thienyl)methylmethyl-2-propenoic acid;
2-n-butyl-5,6-dichloro-1-(2-chlorophenyl)methyl-1H-benzimidazole-7-carboxylic acid;
2-[2-n-butyl-1-(2-chlorophenyl)methyl-1H-benzimidazol-7-yl]acetic acid;
L-α-amino-N-[2-n-butyl-1-(2-chlorophenyl)methyl-1H-benzimidazole-7-ethyl]-2-(2-thienyl)methylpropionic acid;
1-(2-chlorophenyl)methyl-2-heptafluoropropyl-1H-benzimidazole-6-carboxylic acid;

L-α-amino-N-(2-n-butyl-1H-benzimidazole-1-propanoyl)-2-(2-thienyl)methylpropanoic acid;

L-α-amino-N-(2-n-butyl-1H-benzimidazole-1-acetoyl)-2-(2-thienyl)methylpropionic acid;

L-α-N-[2-n-butyl-1-(2-chlorophenyl)methyl-1H-benzimidazole-7-acetoyl]-2-(2-thienyl)methylpropionic acid;

methyl L-α-amino-N-(2-n-butyl-1H-benzimidazole-1-propanoyl)-2-(2-thienyl)methylpropanoate;

2-n-butyl-6-chloro-1-(2-chlorophenyl)methyl-1H-benzimidazole-7-carboxylic acid;

2-n-butyl-1-(4-carboxyphenyl)-5-chloro-1H-benzimidazole-7-carboxylic acid;

1-(4-carboxyphenyl)methyl-6-chloro-1H-benzimidazole-7-carboxylic acid;

2-n-butyl-1-(4-carboxyphenyl)ethyl-5-chloro-1H-benzimidazole-7-carboxylic acid;

2-n-butyl-1-(4-carboxyphenyl)methyl-5-chloro-4-methyl-1H-benzimidazole-7-carboxylic acid; or 2-n-butyl-5-chloro-1-(2-chlorophenyl)methyl-1H-benzimidazole-7-carboxylic acid.

17. A method of treating hypertension in mammals which comprises administering to a subject in need thereof an effective amount of a compound of claim 1.

18. A method of treating congestive heart failure in mammals which comprises administering to a subject in need thereof an effective amount of a compound of claim 1.

19. A method of treating renal failure in mammals which comprises administering to a subject in need thereof an effective amount of a compound of claim 1.

20. A method of treating glaucoma in mammals which comprises administering to a subject in need thereof an effective amount of a compound of claim 1.

* * * * *